(12) United States Patent
Holland et al.

(10) Patent No.: US 7,454,314 B2
(45) Date of Patent: Nov. 18, 2008

(54) MEDICATION MANAGEMENT SYSTEM

(75) Inventors: Geoffrey N. Holland, Wadsworth, IL (US); Patrick B. Keely, Grayslake, IL (US); Jeff Pelletier, Fox River Grove, IL (US); Charles P. Moran, Colleyville, TX (US); John W. Huang, Hillsborough, CA (US); Marwan Fathallah, Mundelein, IL (US); Martin A. McNeela, Encinitas, CA (US)

(73) Assignee: Hospira, Inc., Lake Forest, IL (US)

( * ) Notice: Subject to any disclaimer, the term of this patent is extended or adjusted under 35 U.S.C. 154(b) by 0 days.

(21) Appl. No.: 11/591,970

(22) Filed: Nov. 2, 2006

(65) Prior Publication Data
US 2007/0083344 A1    Apr. 12, 2007

Related U.S. Application Data

(62) Division of application No. 10/783,642, filed on Feb. 20, 2004.

(60) Provisional application No. 60/509,404, filed on Oct. 7, 2003, provisional application No. 60/527,583, filed on Dec. 5, 2003.

(51) Int. Cl.
  *G06F 11/30* (2006.01)
  *G06F 15/00* (2006.01)
(52) U.S. Cl. .................................... 702/182
(58) Field of Classification Search ................ 702/182
  See application file for complete search history.

(56) References Cited

U.S. PATENT DOCUMENTS

| | | | |
|---|---|---|---|
| 4,696,671 A | 9/1987 | Epstein et al. |
| 4,731,051 A | 3/1988 | Fischell |
| 4,785,969 A | 11/1988 | McLaughlin |
| 4,908,017 A | 3/1990 | Howson et al. |
| 4,978,335 A | 12/1990 | Arthur, III |
| 5,058,161 A | 10/1991 | Weiss |
| 5,088,981 A | 2/1992 | Howson et al. |
| 5,097,505 A | 3/1992 | Weiss |
| 5,153,827 A | 10/1992 | Coutre et al. |

(Continued)

FOREIGN PATENT DOCUMENTS

DE    199 32 147    7/1999

(Continued)

*Primary Examiner*—Michael P. Nghiem
*Assistant Examiner*—Cindy H Khuu
(74) *Attorney, Agent, or Firm*—Michael R. Crabb

(57) ABSTRACT

A medication management system (MMS) includes a medication management unit (MMU) associated with a medical device. The MMU downloads a medication order to the medical device only if information from a first input matches information from a second input. The medical device receives delivery information only from the MMU. The medication order is performed only after delivery data validation. The MMU also determines drug-drug incompatibility. The MMU can modulate (start, stop, and dynamically adjust) medication order performance. The medical device wirelessly receives a patient ID to automatically associate with the patient. During delivery, the medical device caches an updated drug library to replace an existing one. The medical device displays a patient picture for validation. The MMU evaluates the performance of medical devices and caregivers based medical device feedback. The MMU adjusts the output of medical device information conveyed to a caregiver.

8 Claims, 25 Drawing Sheets

U.S. PATENT DOCUMENTS

| | | | |
|---|---|---|---|
| 5,161,222 A | 11/1992 | Montejo et al. | |
| 5,317,506 A | 5/1994 | Coutre et al. | |
| 5,319,363 A | 6/1994 | Welch et al. | |
| 5,338,157 A | 8/1994 | Blomquist | |
| 5,378,231 A | 1/1995 | Johnson et al. | |
| 5,417,222 A | 5/1995 | Dempsey et al. | |
| 5,445,621 A | 8/1995 | Poli et al. | |
| 5,455,851 A | 10/1995 | Chaco et al. | |
| 5,465,082 A | 11/1995 | Chaco | |
| 5,485,408 A | 1/1996 | Blomquist | |
| 5,507,288 A | 4/1996 | Bocker et al. | |
| 5,507,786 A * | 4/1996 | Morgan et al. | 607/27 |
| 5,522,798 A | 6/1996 | Johnson et al. | |
| 5,547,470 A | 8/1996 | Johnson et al. | |
| 5,594,786 A | 1/1997 | Chaco et al. | |
| 5,620,608 A | 4/1997 | Rosa et al. | |
| 5,630,710 A | 5/1997 | Tune et al. | |
| 5,643,212 A | 7/1997 | Coutre et al. | |
| 5,658,250 A | 8/1997 | Blomquist et al. | |
| 5,669,877 A | 9/1997 | Blomquist | |
| 5,681,285 A | 10/1997 | Ford et al. | |
| 5,689,229 A | 11/1997 | Chaco et al. | |
| 5,778,256 A | 7/1998 | Darbee | |
| 5,781,442 A | 7/1998 | Engleson et al. | |
| 5,788,669 A | 8/1998 | Peterson | |
| 5,814,015 A | 9/1998 | Gargano et al. | |
| 5,827,179 A | 10/1998 | Lichter et al. | |
| 5,832,448 A | 11/1998 | Brown | |
| 5,836,910 A | 11/1998 | Duffy et al. | |
| 5,850,344 A | 12/1998 | Conkright | |
| 5,867,821 A | 2/1999 | Ballantyne et al. | |
| 5,871,465 A | 2/1999 | Vasko | |
| 5,897,493 A | 4/1999 | Brown | |
| 5,915,240 A | 6/1999 | Karpf | |
| 5,924,074 A | 7/1999 | Evans | |
| 5,935,099 A | 8/1999 | Peterson et al. | |
| 5,971,594 A | 10/1999 | Sahai et al. | |
| 5,975,081 A | 11/1999 | Hood et al. | |
| 5,997,476 A | 12/1999 | Brown | |
| 6,003,006 A | 12/1999 | Colella et al. | |
| 6,012,034 A | 1/2000 | Hamparian et al. | |
| 6,021,392 A | 2/2000 | Lester et al. | |
| 6,024,539 A | 2/2000 | Blomquist | |
| 6,032,676 A | 3/2000 | Moore | |
| 6,073,106 A | 6/2000 | Rozen et al. | |
| 6,104,295 A | 8/2000 | Gaisser et al. | |
| RE36,871 E | 9/2000 | Epstein et al. | |
| 6,150,942 A | 11/2000 | O'Brien | |
| 6,157,914 A | 12/2000 | Seto et al. | |
| 6,159,147 A | 12/2000 | Lichter et al. | |
| 6,182,667 B1 | 2/2001 | Hanks et al. | |
| 6,189,105 B1 | 2/2001 | Lopes | |
| 6,195,589 B1 | 2/2001 | Ketcham | |
| 6,234,176 B1 | 5/2001 | Domae et al. | |
| 6,241,704 B1 | 6/2001 | Peterson et al. | |
| 6,248,067 B1 | 6/2001 | Causey, III et al. | |
| 6,259,355 B1 | 7/2001 | Chaco et al. | |
| 6,269,340 B1 | 7/2001 | Ford et al. | |
| 6,270,455 B1 | 8/2001 | Brown | |
| 6,277,072 B1 | 8/2001 | Bardy | |
| 6,280,380 B1 | 8/2001 | Bardy | |
| 6,283,761 B1 | 9/2001 | Joao | |
| 6,312,378 B1 | 11/2001 | Bardy | |
| 6,482,158 B2 | 11/2002 | Mault | |
| 6,485,418 B2 | 11/2002 | Yasushi et al. | |
| 6,494,831 B1 | 12/2002 | Koritzinsky | |
| 6,519,569 B1 | 2/2003 | White et al. | |
| 6,544,228 B1 | 4/2003 | Heitmeier | |
| 6,581,117 B1 | 6/2003 | Klein et al. | |
| 6,589,229 B1 | 7/2003 | Connelly et al. | |
| 6,602,191 B2 | 8/2003 | Quy | |
| 6,640,246 B1 | 10/2003 | Gary, Jr. et al. | |
| 6,641,533 B2 | 11/2003 | Causey, III et al. | |
| 6,652,455 B1 | 11/2003 | Kocher | |
| 6,725,200 B1 | 4/2004 | Rost | |
| 6,752,787 B1 | 6/2004 | Causey, III et al. | |
| 6,790,198 B1 | 9/2004 | White et al. | |
| 6,809,653 B1 | 10/2004 | Mann et al. | |
| 2001/0016056 A1 | 8/2001 | Westphal et al. | |
| 2001/0032099 A1 | 10/2001 | Joao | |
| 2001/0037060 A1 | 11/2001 | Thompson et al. | |
| 2001/0044731 A1 | 11/2001 | Coffman et al. | |
| 2002/0032583 A1 | 3/2002 | Joao | |
| 2002/0038392 A1 | 3/2002 | De La Huerga | |
| 2002/0169636 A1 | 11/2002 | Eggers et al. | |
| 2003/0139701 A1 | 7/2003 | White et al. | |
| 2003/0140928 A1* | 7/2003 | Bui et al. | 128/898 |
| 2003/0200116 A1 | 10/2003 | Forrester | |
| 2004/0015132 A1* | 1/2004 | Brown | 604/131 |
| 2008/0004904 A1* | 1/2008 | Tran | 705/2 |
| 2008/0091466 A1* | 4/2008 | Butler et al. | 705/2 |

FOREIGN PATENT DOCUMENTS

| | | |
|---|---|---|
| EP | 0 683 465 | 11/1995 |
| EP | 0 880 936 | 12/1998 |
| EP | 1 197 178 | 4/2002 |
| FR | 2 717 919 | 3/1994 |
| WO | 96/08755 | 3/1996 |
| WO | 98/12670 | 3/1998 |
| WO | 98/19263 | 5/1998 |
| WO | 99/51003 | 10/1999 |
| WO | 01/14974 | 3/2001 |
| WO | 01/33484 | 5/2001 |

* cited by examiner

FIG. 11

MEDICATION MANAGEMENT SYSTEM

CROSS REFERENCE TO RELATED APPLICATIONS

This application is a divisional of U.S. Ser. No. 10/783,642 filed Feb. 20, 2004. This application claims priority based upon U.S. Provisional Application Ser. No. 60/509,404 filed Oct. 7, 2003 and U.S. Provisional Application Ser. No. 60/527,583 filed Dec. 5, 2003, which are expressly incorporated herein by reference in their entirety.

BACKGROUND OF THE INVENTION

The present invention relates to the field of delivering medication to patients, more particularly to an integrated system for maximizing patient safety and caregiver productivity for medication delivery.

Modern medical care often involves the use of medical pump devices to deliver fluids and/or fluid medicine to patients. Medical pumps permit the controlled delivery of fluids to a patient, and such pumps have largely replaced gravity flow systems, primarily due to the pump's much greater accuracy in delivery rates and dosages, and due to the possibility for flexible yet controlled delivery schedules. However, modern medical devices, including medical pumps, can be complicated and time-consuming for caregivers to program. Medical facilities struggle to provide appropriate caregiver staffing levels and training while holding down the cost of medical care. Human errors in pump programming and other medication errors can have adverse or even deadly consequences for the patient.

Therefore, a principal object of this invention is to provide an integrated medication management system that reduces the risks of medication error and improves patient safety.

A further object of the invention is to provide a medication management system that improves caregiver productivity.

Another object of the invention is to provide a medication management system that improves the accuracy of the medication delivery process by eliminating labor-intensive tasks that can lead to human errors.

A still further object of the invention is to provide a medication management system that relies on an electronically-transmitted medication order and machine readable indicia on the drug container, patient, and medication delivery device to insure the "five rights" of medication management, i.e., that the right medication is delivered to the right patient through the right route in the right dosage at the right time.

Another object of the invention is to provide the caregiver with a pass code or machine-readable indicia to insure that only an authorized individual caregiver can initiate a medication order and that an authorized caregiver must confirm the medication order prior to its administration to the patient.

A still further object of the invention is to provide a medication management system wherein the medical device receives delivery information electronically only through a medication management unit.

Another object of the invention is to provide medication management system wherein the medical device is preprogrammed and executes the medication order only after a user has validated delivery data.

A still further object of the invention is to provide a medication management system wherein the physical location of a medical device can be determined and pinpointed based on the last access node used by the medical device.

Another object of the invention is to provide a medication management system for adjusting a patient-specific rule set based on new patient conditions and/or recent lab results.

A still further object of the invention is to provide a medication management system for determining drug-drug incompatibility between two medication orders for concurrent delivery (to the same patient at the same time) and/or in an unacceptably close time sequence.

Another object of the invention is to provide a medication management system for remotely sending an order or information to the medical device to modulate a planned or ongoing medication order and delivery thereof to the patient.

A still further object of the invention is to provide a medication management system for automatically associating a medical device with a patient based on wireless transmission of a patient ID to the medical device, thereby establishing a patient area network.

Another object of the invention is to provide a medication management system for caching an updated drug library at the medical device to replace an existing drug library, during execution of a medication order.

A still further object of the invention is to provide a medication management system for displaying a picture of the patient on a device within the system, such as at the medical device, for a caregiver to perform a visual validation of the right patient.

Another object of the invention is to provide a medication management system for evaluating the performance of multiple medical devices based on information from the multiple medical devices.

A still further object of the invention is to provide a medication management system for evaluating the performance of one or more caregivers based on information from multiple medical devices.

Another object of the invention is to provide a medication management system for adjusting medical device output conveyed to a caregiver based on multiple factors.

These and other objects will be apparent to those skilled in the art.

SUMMARY OF THE INVENTION

A medication management system includes a medication management unit (MMU) associated with a medical device for performing a prescribed medication order. The MMU compares medication order information from a first input means to machine readable delivery information from a second input means and downloads a medication order to the medical device only if the information from the first input means matches the information from the second input means. The medical device receives medication order information electronically only through the medication management unit (i.e., does not receive delivery information directly from the second input means). The MMU permits the medical device to perform the order only after a user has validated delivery data at the medical device.

The MMU determines the general physical location of a medical device based on the last access node used by the wireless connectivity capability in the medical device and an audible alarm can be activated to allow a user to pinpoint the physical location of the medical device more precisely.

Using expert clinical support decision rules, the MMU also determines drug-drug incompatibility between two medication orders for concurrent delivery (to the same patient at the same time) and/or in an unacceptably close time sequence through the same output IV line. Further, the MMU also adjusts patient-specific rule sets based on newly measured or observed patient conditions and/or recent lab results. Advantageously, warnings, alarms or alerts based on violations of these rules are provided as close as possible to the actual delivery time so that they are more meaningful, ripe for corrective action, and less likely to be ignored due to incomplete information.

Based on laboratory data or other newly received patient information, the MMU can modulate the medication order planned or currently being delivered. The MMU sends an order from the MMU to the medical device to modulate performance of the medication order. The patient and the medical device automatically associate with each other to form a patient area network based on wireless transmission of ID information. During execution of a medication order, the medical device caches an updated drug library in a cache memory and, upon occurrence of a triggering event, replaces an existing drug library in the primary memory of the device with the updated library. A picture of the patient is displayed at a device within the system, such as the medical device, for a caregiver to perform a visual validation of the right patient. The MMU evaluates the performance of multiple medical devices and one or more caregivers based on information communicated from the medical devices. The MMU adjusts medical device output conveyed to a caregiver based on multiple factors.

DESCRIPTION OF THE DRAWINGS

FIG. 11 is a screen shot of a delivery information input device displaying a medication order prescribed for a patient;

DETAILED DESCRIPTION OF THE PREFERRED EMBODIMENT

Figure 1:
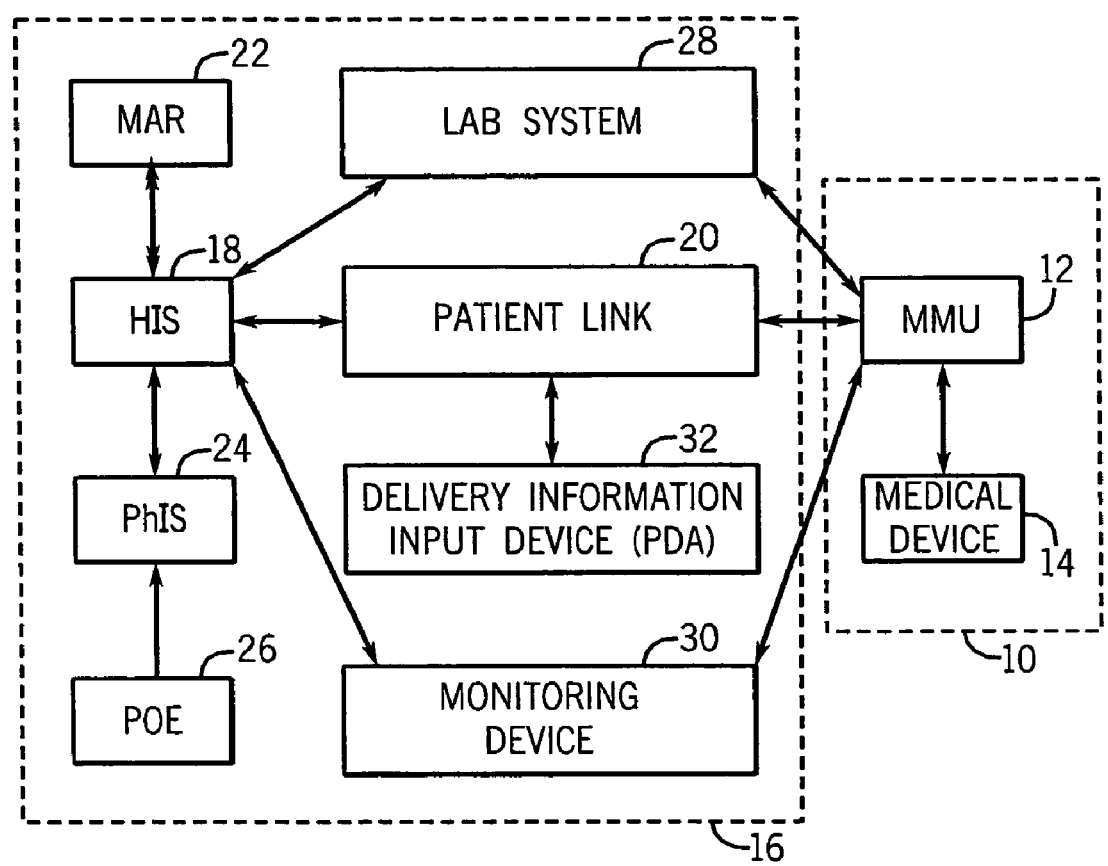
FIG. 1 is a schematic diagram of the medication management system including a medication management unit and a medical device, integrated with an information system, according to the present invention.

With reference to FIG. 1, the medication management system (MMS) 10 of the present invention includes a medication management unit (MMU) 12 and a medical device 14, typically operating in conjunction with one or more information systems or components of a hospital environment 16. The term hospital environment should be construed broadly herein to mean any medical care facility, including but not limited to a hospital, treatment center, clinic, doctor's office, day surgery center, hospice, nursing home, and any of the above associated with a home care environment. As discussed below, there can be a variety of information systems in a hospital environment As shown in FIG. 1, MMU 12 communicates to a hospital information system (HIS) 18 via a caching mechanism 20 that is part of the hospital environment 16.

It will be understood by those of skill in art that the caching mechanism 20 is primarily a pass through device for facilitating communication with the HIS 18 and its functions can be eliminated or incorporated into the MMU 12 and/or the medical device 14 and/or the HIS 18 and/or other information systems or components within the hospital environment 16. The Caching Mechanism 20 provides temporary storage of hospital information data separate from the HIS 18, the medication administration record system (MAR) 22, pharmacy information system (PhIS) 24, physician order entry (POE) 26. and/or Lab System 28. The Caching Mechanism 20 provides information storage accessible to the Medication Management System 10 to support scenarios where direct access to data within the hospital environment 16 is not available or not desired. For example, the caching mechanism 20 provides continued flow of information in and out of the MMU 12 in instances where the HIS 18 down or the connectivity between the MMU 12 and the electronic network (not shown) is down. The caching mechanism 20 also provides improved response time to queries from the MMU 12 to the HIS 18, as direct queries to the HIS 18 are not consistently processed at the same speed and often require a longer period of time far the HITS 18 to process.

The HIS 18 communicates with a medication administration record system (MAR) 22 for maintaining medication records and a pharmacy information system (PhIS) 24 for delivering drug orders to the HIS. A physician/provider order entry (POE) device 26 permits a healthcare provider to deliver a medication order prescribed for a patient to the hospital information system directly or indirectly via the PhIS 24. One skilled in the art will also appreciate that a medication order can be sent to the MMU 12 directly from the PhIS 24 or POE device 26. As used herein the term medication order is defined as an order to administer something that has a physiological impact on a person or animal, including but not limited to liquid or gaseous fluids, drugs or medicines, liquid nutritional products and combinations thereof.

Lab system 28 and monitoring device 30 also communicate with the MMU 12 to deliver updated patient-specific information to the MMU 12. For example, the lab system 28 sends lab results of blood work on a specific patient to the MMU 12, while the monitoring device 30 sends current and/or logged monitoring information such as heart rate to the MMU 12. As shown, the MMU 12 communicates directly to the lab system 28 and monitoring device 30. However, it will be understood to those of skill in art that the MMU 12 can communicate to the lab system 28 and monitoring device 30 indirectly via the HIS 18, the caching mechanism 20, the medical device 14 or some other intermediary device or system. This real-time or near delivery time patient-specific information is useful in adapting patient therapy because it may not have been available at the time the medication order was prescribed. As used herein, the term real-time denotes a response time with a latency of less than 3 seconds. The real-time digital communications between the MMU 12 and other interconnected devices and networks prevents errors in patient care before administration of medications to the patient, especially in the critical seconds just prior to the start of medication delivery.

Delivery information input device 32 also communicates with the MMU 12 to assist in processing drug orders for delivery through the MMU 12. The delivery information input device 32 can be any sort of data input means, including those adapted to read machine readable indicia such as barcode labels; for example a personal digital assistant (PDA) with a barcode scanner. Hereinafter the delivery information input device 32 will be referred to as input device 32. Alternatively, the machine readable indicia may be in other known forms, such as radio frequency identification (RFID) tag, two-dimensional bar code, ID matrix, transmitted radio ID code, human biometric data such as fingerprints, etc. and the input device 32 adapted to "read" or recognize such indicia. The input device 32 is shown as a separate device from the medical device 14; alternatively, the input device 32 communicates directly with the medical device 14 or may be integrated wholly or in part with the medical device.

Figure 2:
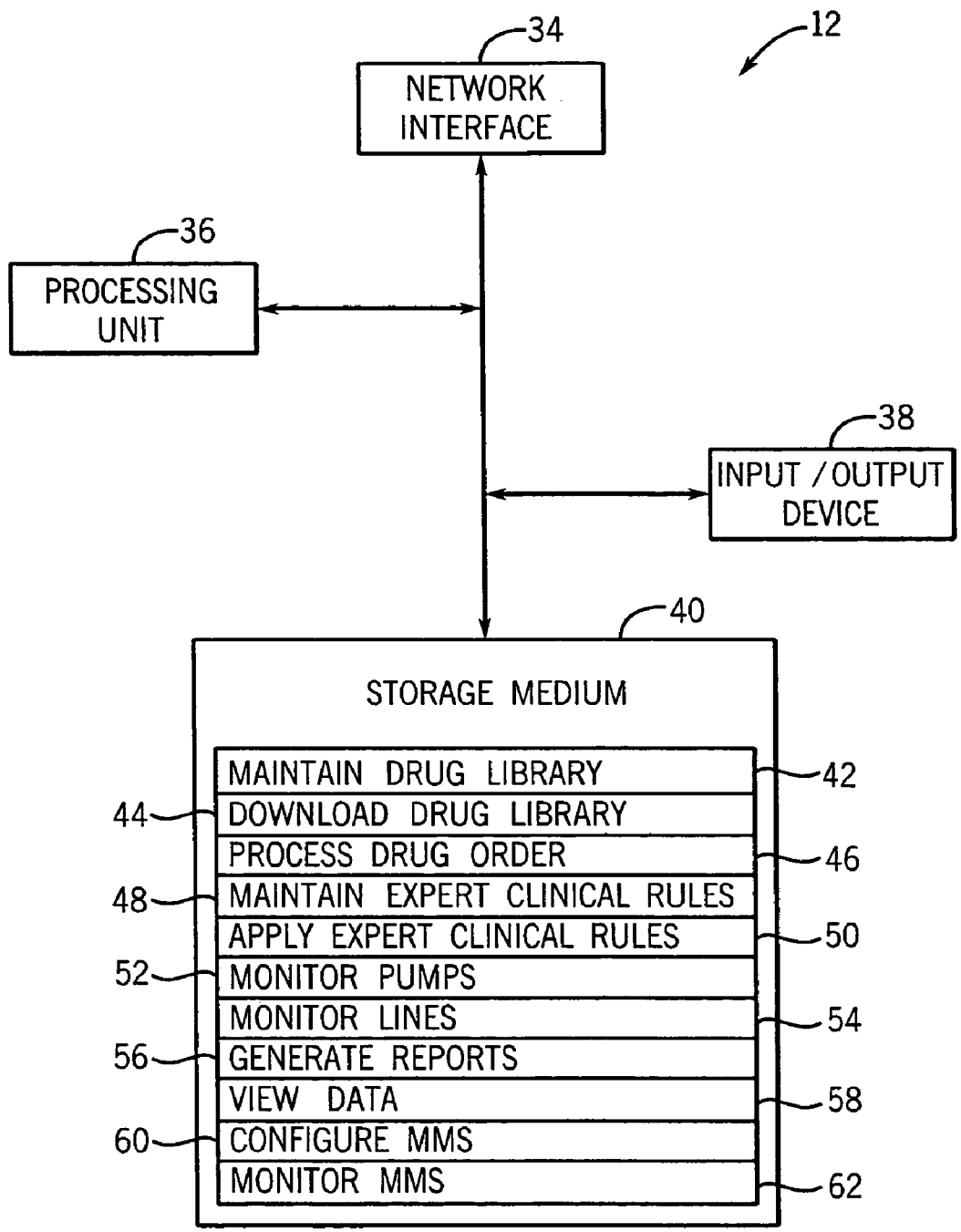
FIG. 2 is a schematic diagram of the medication management unit according to the invention.

With reference to FIG. 2, the medication management unit 12 includes a network interface 34 for connecting the MMU 12 to multiple components of a hospital environment 16, the medical device 14, and any other desired device or network. A processing unit 36 is included in MMU 12 and performs various operations described in greater detail below. A display/input device 38 communicates with the processing unit 36 and allows the user to receive output from processing unit 36 and/or input information into the processing unit 36. Those of ordinary skill in the art will appreciate that display/input device 38 may be provided as a separate display device and a separate input device.

An electronic storage medium 40 communicates with the processing unit 36 and stores programming code and data necessary for the processing unit 36 to perform the functions of the MMU 12. More specifically, the storage medium 40 stores multiple programs formed in accordance with the present invention for various functions of the MMU 12 including but not limited to the following programs: Maintain Drug Library 42; Download Drug Library 44; Process Drug Order 46; Maintain Expert Clinical Rules 48; Apply Expert Clinical Rules 50; Monitor Pumps 52; Monitor Lines 54; Generate Reports 56; View Data 58; Configure the MMS 60; and Monitor the MMS 62. The Maintain Drug Library 42 program creates, updates, and deletes drug entries and, establishes a current active drug library. The Download Drug Library 44 program updates medical devices 14 with the current drug library. The Process Drug Order 46 program processes the medication order for a patient, verifying that the point of care (POC) medication and delivery parameters match those ordered. The Maintain Expert Clinical Rules 48 program creates, updates, and deletes the rules that describe the hospital's therapy and protocol regimens. The Apply Expert Clinical Rules 50 program performs logic processing to ensure safety and considers other infusions or medication orders, patient demographics, and current patient conditions that include blood chemistry values such as insulin/glucose, monitored data such as pulse and respiration, and clinician assessments such as pain or responsiveness. The Monitor Pumps 52 program acquires ongoing updates of status, events, and alarms transmitted both real-time and in batch mode, as well as tracking the location, current assignment, and software versions such as the drug library version residing on medical device 14. The Monitor Lines 54 program acquires ongoing updates of status, events and alarms for each channel or line for a medical device 14 that supports multiple drug delivery channels or lines. The Generate Reports 56 program provides a mechanism that allows the user to generate various reports of the data held in the MMU storage medium 40. The View Data 58 program provides a mechanism that supports various display or view capabilities for users of the MMU 12. The Notifications 59 program provides a mechanism for scheduling and delivery of events to external systems and users. The Configure the MMS 60 program provides a mechanism for system administrators to install and configure the MMS 10. The Monitor the MMS 62 program enables information technology operations staff capabilities to see the current status of MMS 10 components and processing, and other aspects of day-to-day operations such as system start up, shut down, backup and restore.

Figure 3:
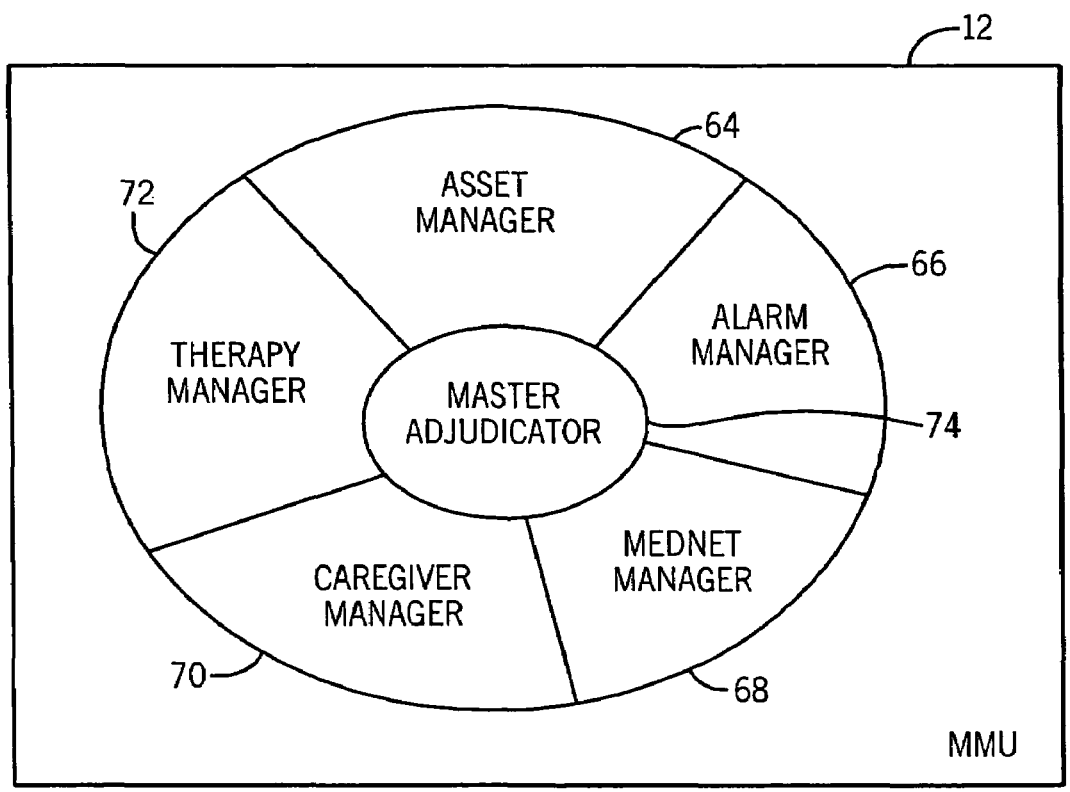
FIG. 3 is a schematic diagram illustrating some of the major functions performed by the medication management unit according to the invention.

With reference to FIG. 3, the various functional programs 42-62 of the MMU 12, each including separate features and rules, are partitioned (at a higher level than shown in FIG. 2) and logically organized into interrelated managing units of the MMU 12. As shown, the MMU 12 includes an asset manager 64, an alarm manager 66, a drug library manager (such as, for example, ABBOTT MEDNET™) 68, a caregiver manager 70, a therapy manager 72, and/or a clinical data manager 73. However, one of ordinary skill in the art will appreciate that additional or alternative hospital system managing units can be provided without departing from the present invention. Additionally, the MMU 12 includes a master adjudicator 74 between the separate interrelated hospital system managing units 64-73 of the MMU 12, to regulate the interaction between the separate management units.

Further, while the MMU 12 as described herein appears as a single device, there may be more than one MMU 12 operating harmoniously and sharing the same database. For example the MMU 12 can consist of a collection of MMU specific applications running on distinct servers in order to avoid a single point of failure, address availability requirements, and handle a high volume of requests. In this example, each individual server portion of the MMU 12 operates in conjunction with other server portions of the MMU 12 to redirect service requests to another server portion of the MMU 12. Additionally, the master adjudicator 74 assigns redirected service requests to another server portion of the MMU 12, prioritizing each request and also ensuring that each request is processed.

With reference to FIGS. 2 and 3, the managing units 64-72 each include separate features and rules to govern their operation. For example the asset manager 64 governs the execution of the Monitor Pumps 52 and Monitor Lines 54 programs; the drug library manager 68 governs the execution of the Drug Library 42 and Download Drug Library 44 programs; the therapy manager 72 governs the execution of the Process Drug Order 46, Maintain Expert Clinical Rules 48, and Apply Expert Clinical Rules 50 programs; and the clinical data manager 73 governs the execution of the Generate Reports 56 and View Data 58 programs. Other distribution of the functional MMU programs 42-62 among the hospital system managing units 64-73 can be made in accordance with the present invention.

Figure 4:
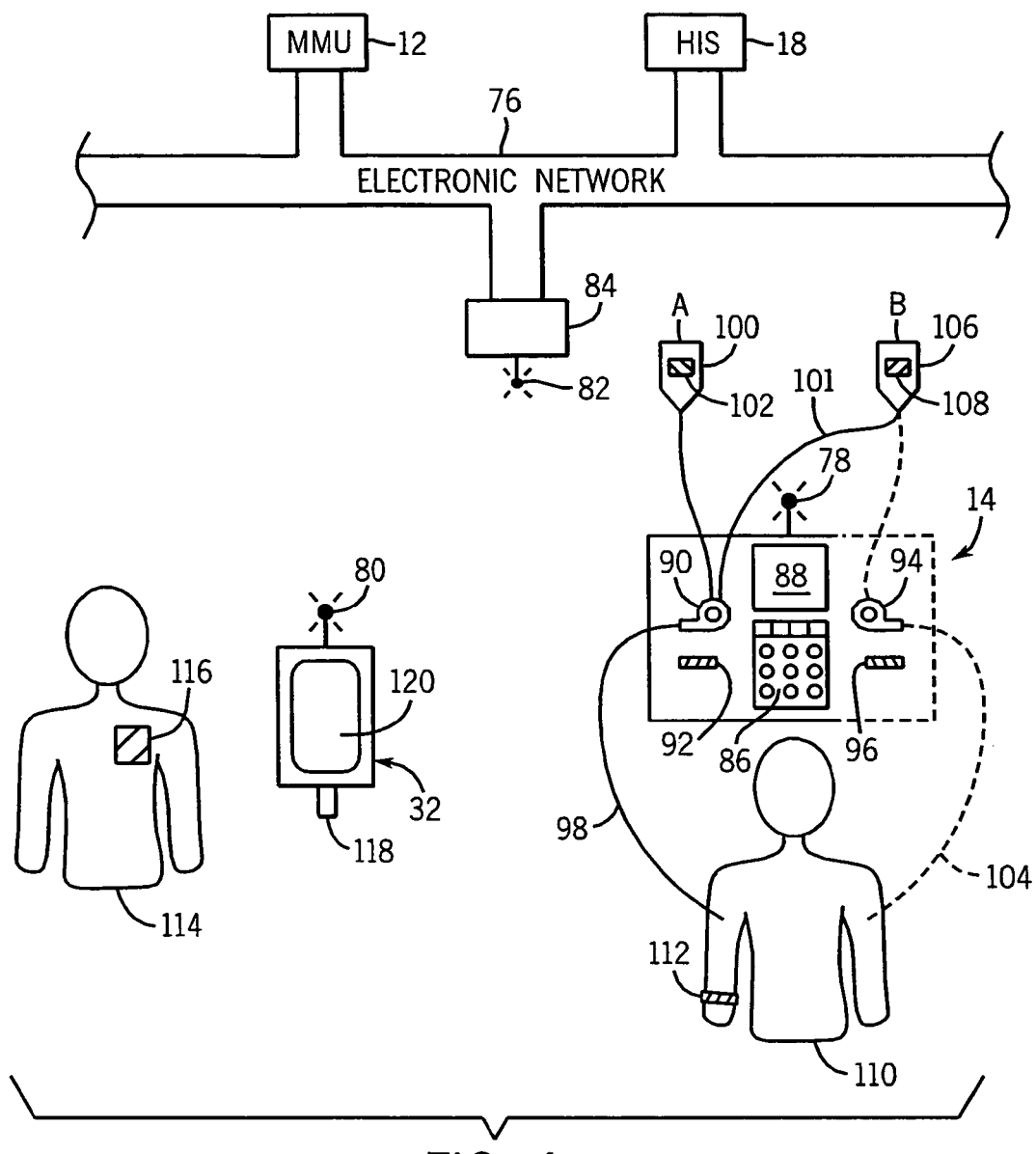
FIG. 4 is a pictorial schematic diagram of the medication management system and its interaction with medical devices and an information system in a hospital environment.

With reference to FIG. 4, an electronic network 76 connects the MMU 12, medical device 14, HIS 18, and input device 32 for electronic communication. The electronic network 76 can be a completely wireless network, a completely hard wired network, or some combination thereof. The medical device 14 and input device 32 are located in a treatment location 77. As shown, the medical device 14 and input device 32 are equipped with antennas 78 and 80, respectively. The antennae 78 and 80 provide for wireless communication to the electronic network 76 via an antenna 82 of access node 84 connected to the electronic network 76. Further details on the antenna 78 can be found in commonly assigned co-pending application entitled SYSTEM FOR MAINTAINING DRUG INFORMATION AND COMMUNICATING WITH MEDICATION DELIVERY DEVICES filed on Feb. 20, 2004, which is expressly incorporated herein in its entirety.

In the context of the present invention, the term "medical device" includes without limitation a device that acts upon a cassette, reservoir, vial, syringe, or tubing to convey medication or fluid to or from a patient (for example, an enteral pump, infusion pump, a patient controlled analgesia (PCA) or pain management medication pump, or a suction pump), a monitor for monitoring patient vital signs or other parameters, or a diagnostic device.

For the purpose of exemplary illustration only, the medical device 14 of FIG. 4 is disclosed as a cassette type infusion pump. The pump style medical device 14 includes a user interface means 86, display 88, first channel 90, and first channel machine readable indicator 92. A first IV line 98 has a conventional cassette 99A (not shown) that is inserted into the first channel 90, and includes a medication bag 100 with a machine readable indicator 102. A second IV line 101 is connected to an input port of the cassette 99A, and includes a medication bag 106 with a machine readable indicator 108. A single output IV line 98 is connected to an outlet port of the cassette 99A and connected to a patient 110 who has a machine readable indicator 112 on a wristband, ankle band, badge or similar article that includes patient-specific and or identifying information, including but not limited to patient ID, and demographics.

In an alternative embodiment illustrated by dashed lines in FIG. 4, the medical device 14 is a multi-channel pump having a first channel 90 with first channel machine readable indicator 92 and at least a second channel 94 with a second channel machine readable indicator 96. The line 101 from the medication bag 106 is eliminated and replaced by line 104 with a cassette 99B (not shown) inserted into the second channel 94 and an output line 104 extends from the cassette to the patient. The same type of cassette 99 (not shown) is inserted in the first channel 90. Additional details on such a multi-channel pump and cassette 99A can be found in commonly owned U.S. patent application Ser. No. 10/696,830 entitled MEDICAL DEVICE SYSTEM, which is incorporated by reference herein in its entirety.

Within a patient area network 113 (hereinafter, PAN 113), a caregiver 114 (if present) has a machine readable indicator 116 on a wristband, badge, or similar article and operates the input device 32. The input device 32 includes an input means 118 for reading the machine readable indicators 92, 96, 102, 108, 112, and 116. An input/output device 120 is included on the input device 32. The input/output device 120 allows the user to receive output from the input device 32 and/or input into the input device 32. Those of ordinary skill in the art will appreciate that display/input device 120 may be provided as a separate display device and a separate input device.

Figure 4A:
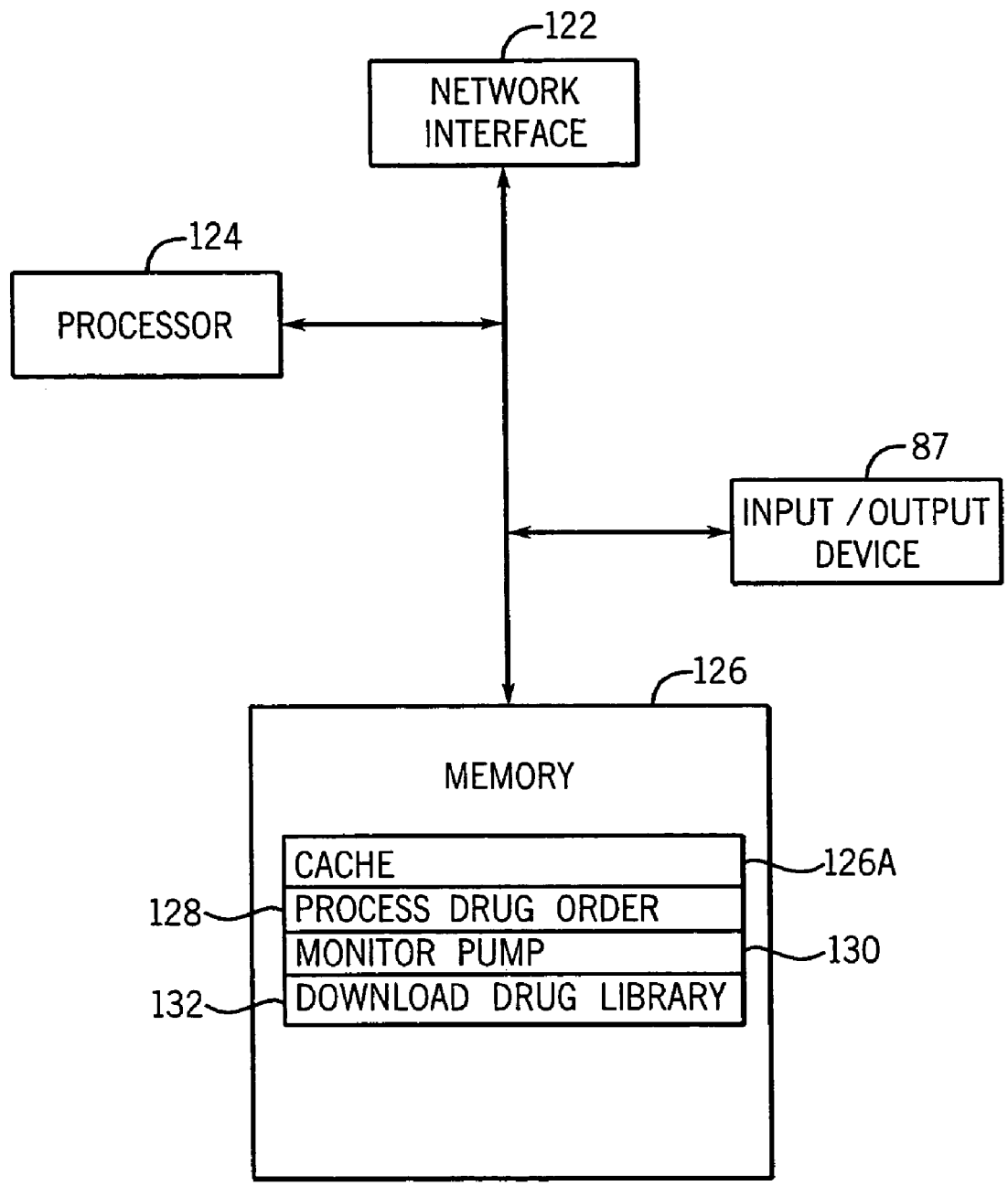
FIG. 4A is a schematic diagram of the medical device according to the invention.

With reference to FIG. 4A, the pump style medical device 14 includes a network interface 122 for connecting the medical device 14 to the electronic network 76. The network interface 122 operates the antenna 78 for wireless connection to the electronic network 76. A processor 124 is included in the medical device 14 and performs various operations described in greater detail below. The input/output device 87(display 88 and user interface means 86) allows the user to receive output from the medical device 14 and/or input information into the medical device 14. Those of ordinary skill in the art will appreciate that input/output device 87 may be provided as a separate display device and a separate input device (as shown in FIG. 4, display 88 and user interface means 86) or combined into a touch screen for both input and output. A memory 126 communicates with the processor 124 and stores code and data necessary for the processor 124 to perform the functions of the medical device 14. More specifically, the memory 126 stores multiple programs formed in accordance with the present invention for various functions of the medical device 14 as is relates to the MMU 12 including the following programs: Process Drug Order 128, Monitor Pump 130, and Download Drug Library 132.

Figure 5:
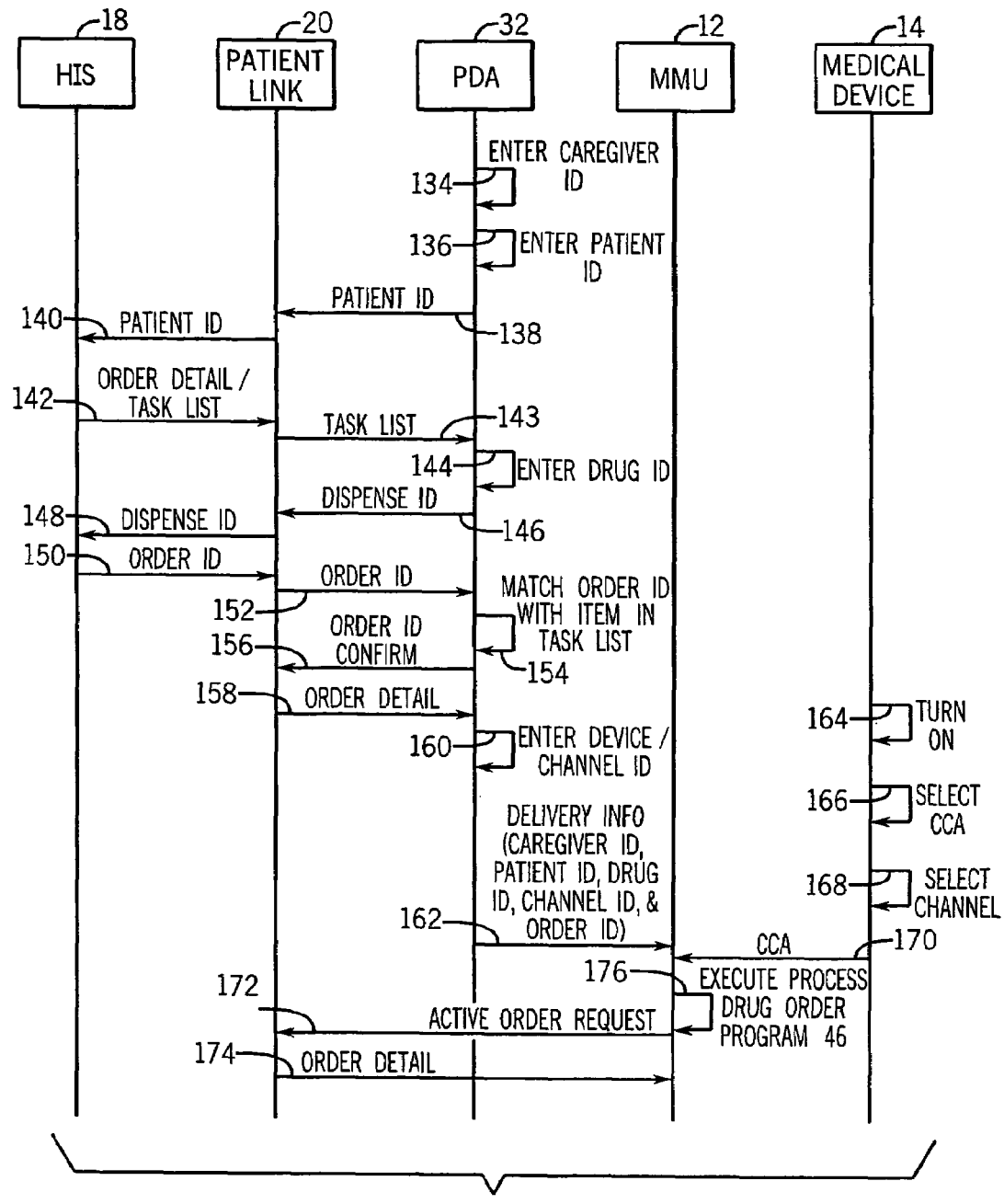
FIG. 5 is a partial flow chart of the medication management system processing a drug order through the medication management unit and medical device, and integrated with an information system according to the invention.
Figure 5A:
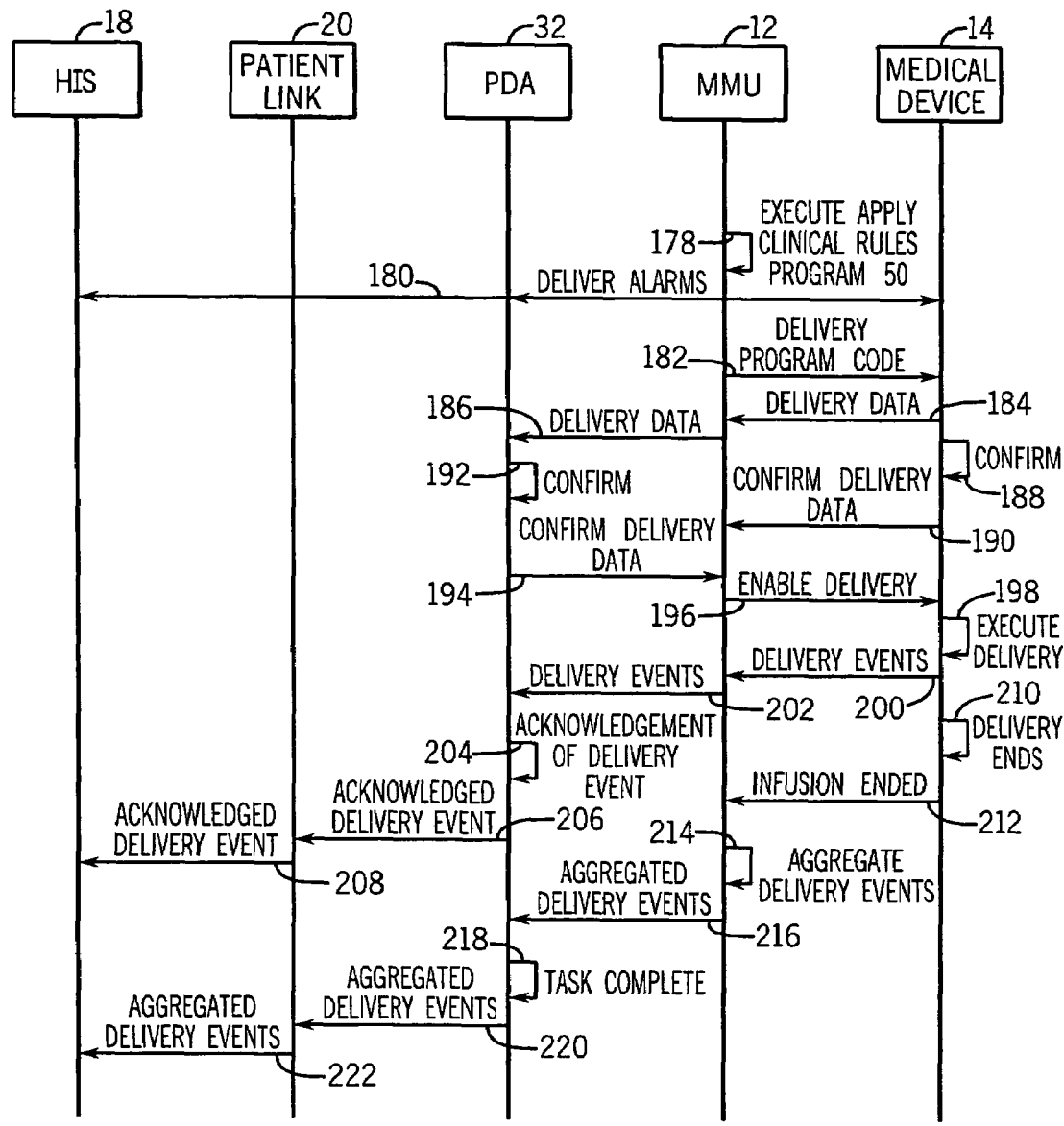
FIG. 5A is a continuation of the flow chart of FIG. 5.

With reference to FIGS. 5 and 5A, the functional steps of the Process Drug Order 46 and Apply Expert Clinical Rules 50 programs of the MMU 12 and the Process Drug Order 128 program of the medical device 14 are shown in operation with the HIS 18, the caching mechanism 20 and the input device 32.

Figure 7:
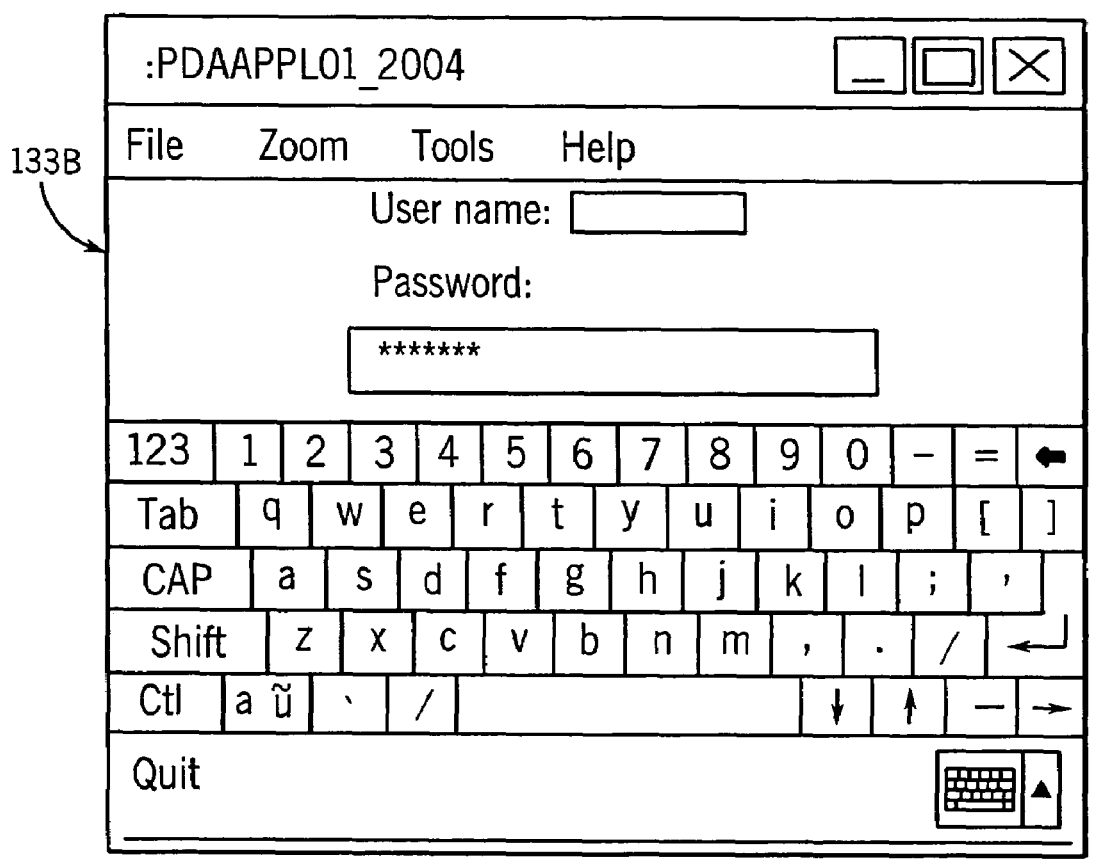
FIG. 7 is a screen shot of a delivery information input device for entry of a caregiver specific pass code.
Figure 8:
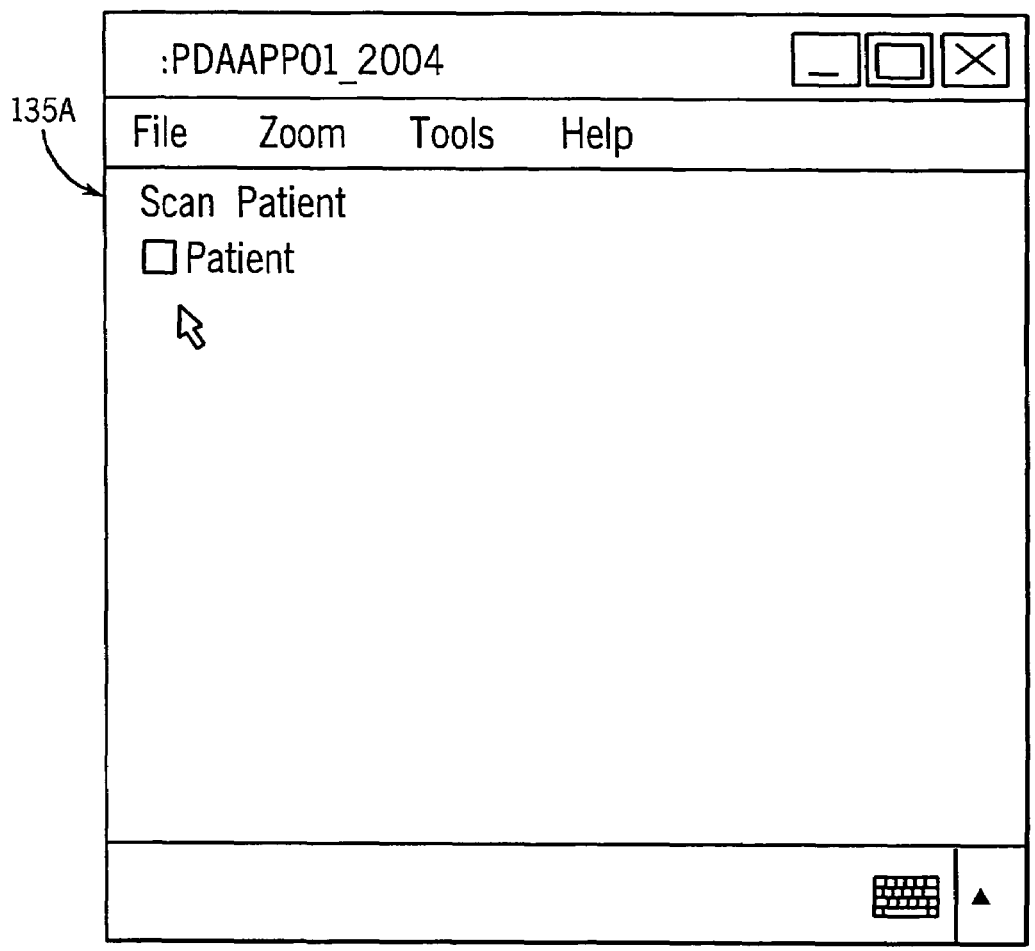
FIG. 8 is a screen shot of a delivery information input device for pulling up a scan patient option.
Figure 9:
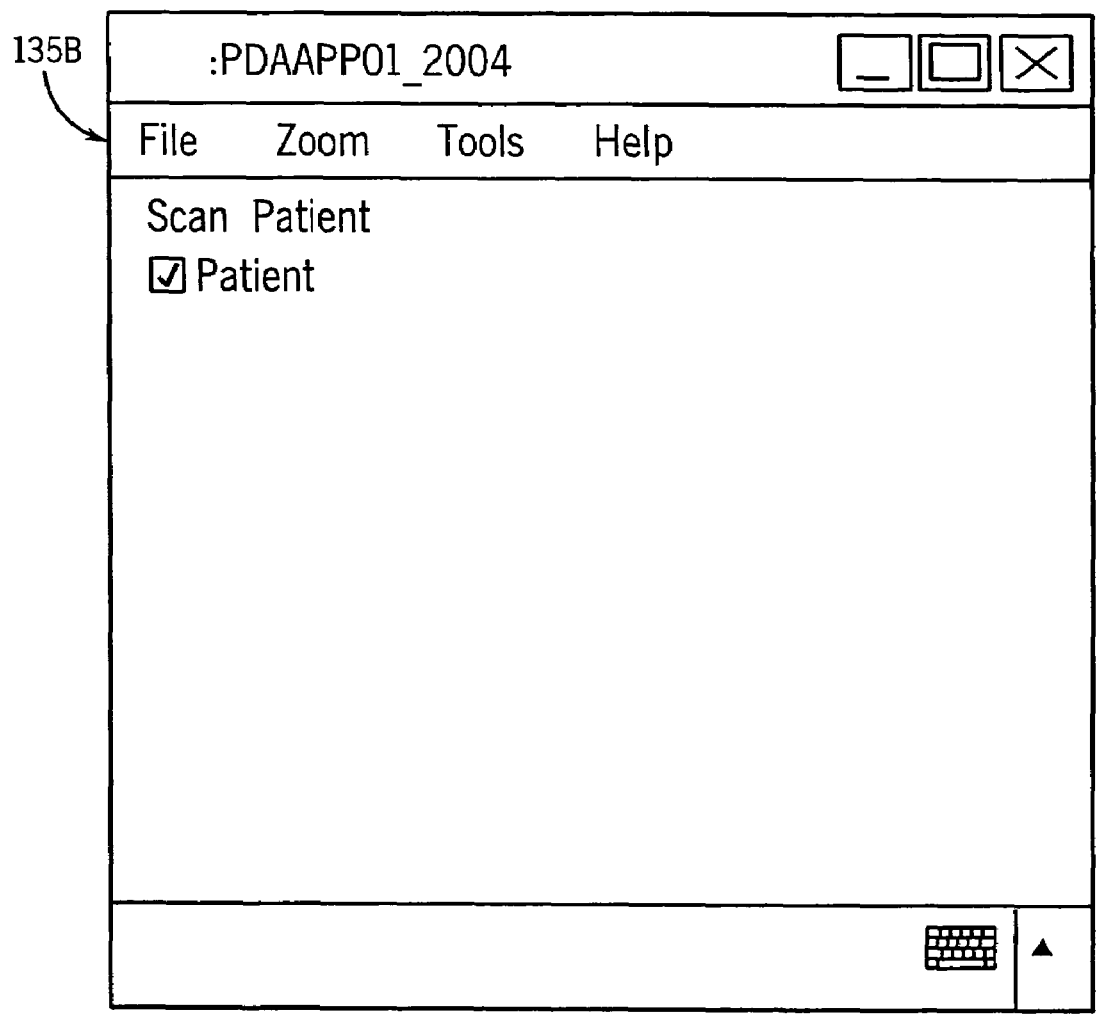
FIG. 9 is a screen shot of a delivery information input device for entry of patient-specific information.
Figure 10:
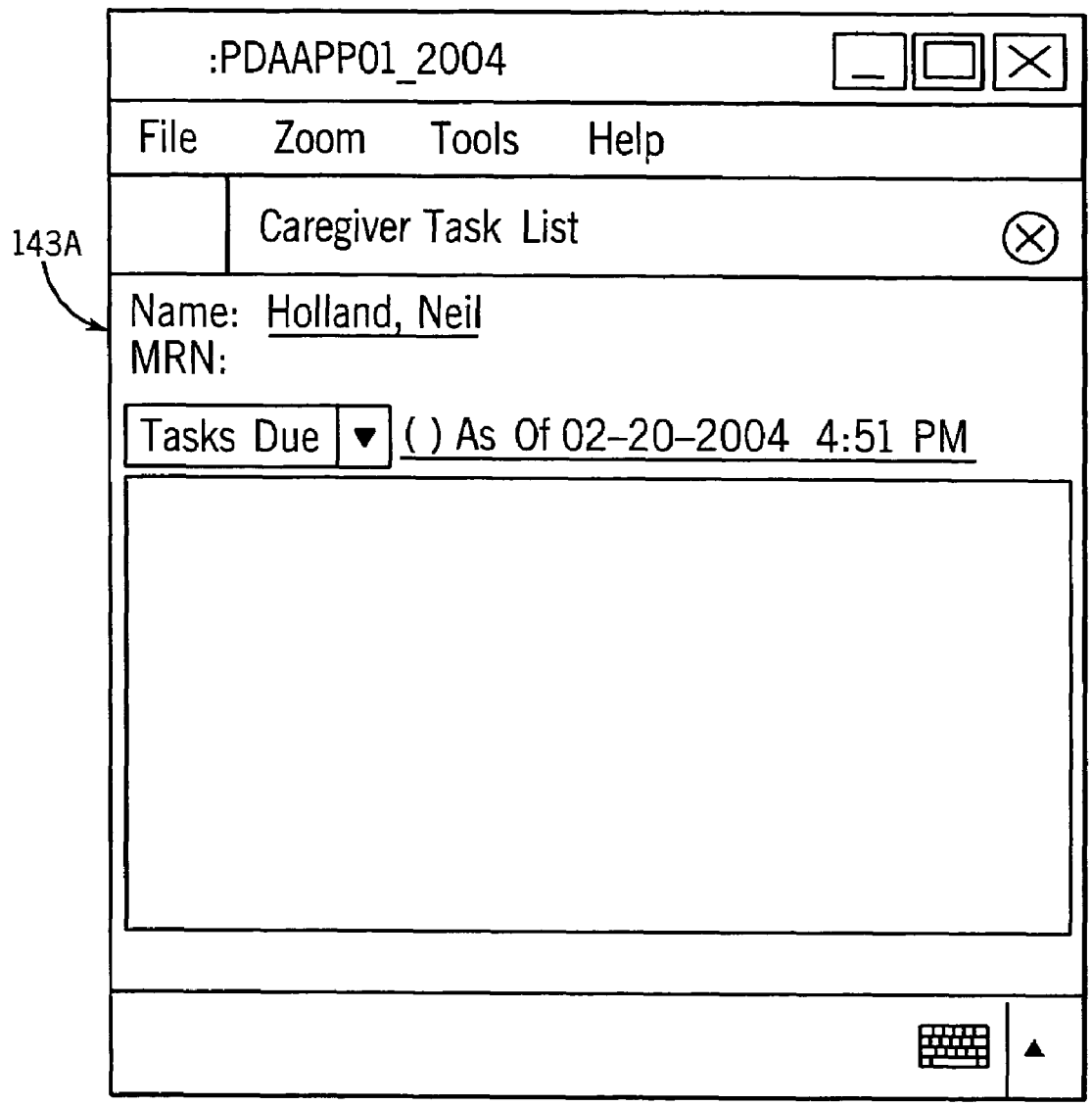
FIG. 10 is a screen shot of a delivery information input device displaying a task list.
Figure 12:
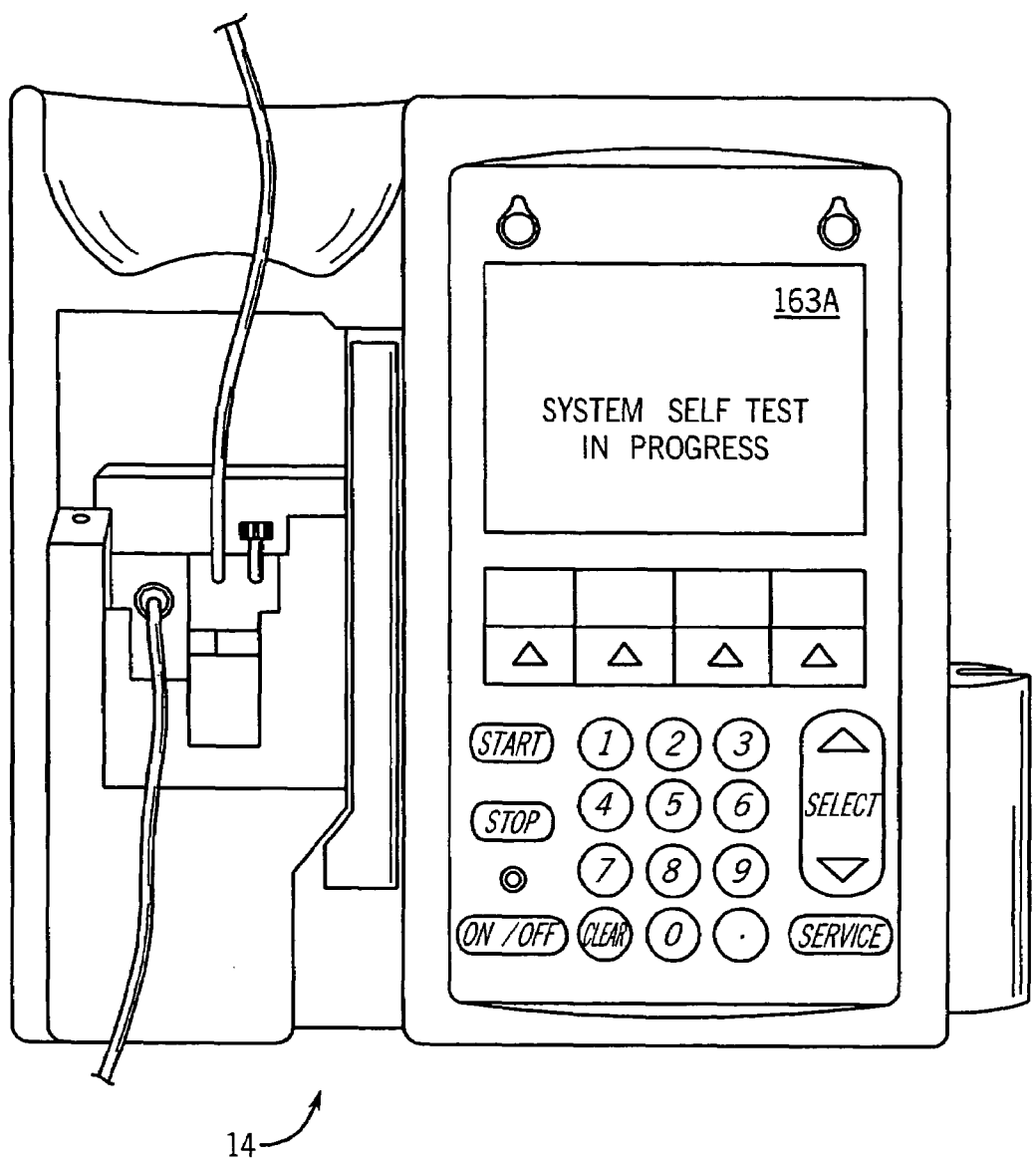
FIG. 12 is a front view of a medical device displaying a start up screen.
Figure 13:
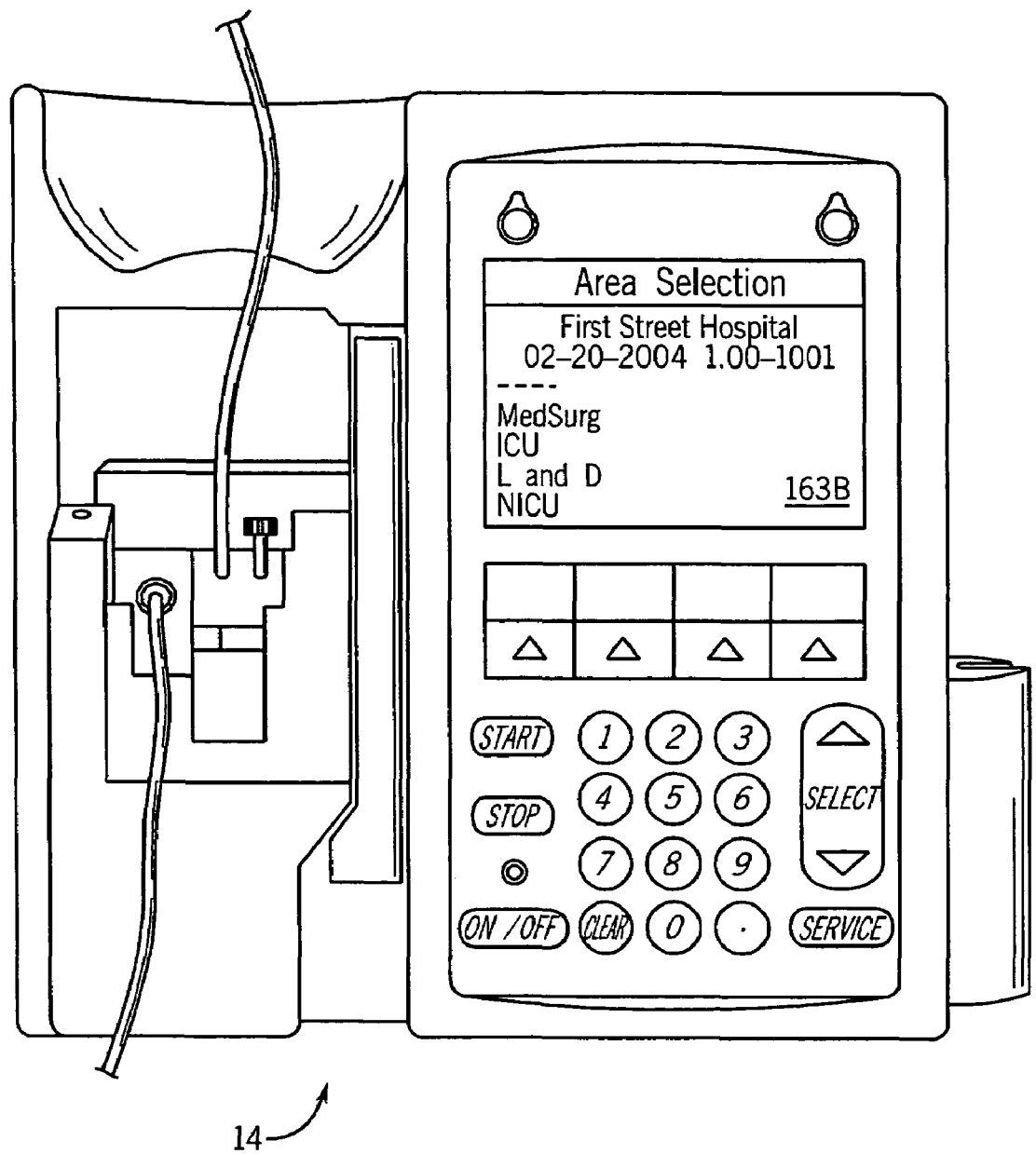
FIG. 13 is a front view of a medical device with a display and user interface means for selecting a clinical care area of a medical facility.
Figure 14:
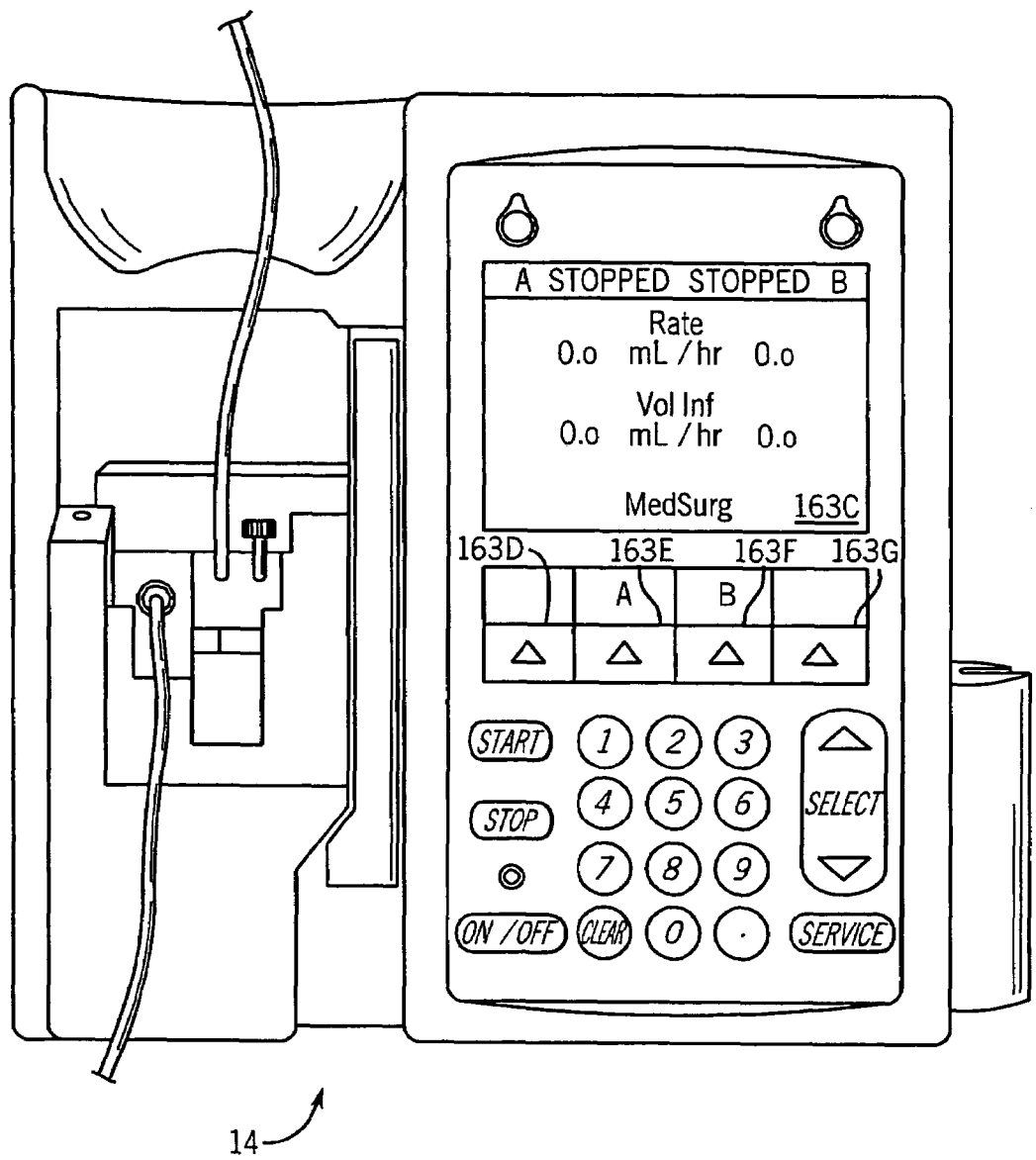
FIG. 14 is a front view of a medical device with a display and user interface means for selecting a desired input channel of the medical device.

With reference to FIGS. 4, 5 and 7, to begin to process a drug order, the input device 32 displays a default screen (not shown) on input/output device 120 which the caregiver uses to access password screen 133B (FIG. 7). The password screen 133B prompts the caregiver 114 to enter caregiver specific identification information (caregiver ID). The caregiver 114 enters caregiver ID such as a username and/or password or pass code, or the machine readable indicator 116. The input device 32 enters this caregiver ID at step 134.

With reference to FIGS. 4, 5 and 8-9, the input device 32 then displays a scan patient screen 135A (FIG. 8) which prompts the caregiver 114 to enter patient-specific identification information (patient ID). The caregiver 114 enters the patient ID such as the machine readable indicator 112. The input device 32 enters this patient ID and at step 136, and displays a confirmed scan patient screen 135B (FIG. 9) indicating that the patient ID was successfully entered into the input device 32.

With reference to FIG. 5, the input device 32 then transmits the patient ID to the caching mechanism 20 at step 138. The caching mechanism 20 transmits the patient ID to the HIS 18 at step 140. The HIS 18 retrieves a patient-specific task list and patient-specific order information based on the patient ID and transmits both to the caching mechanism 20 at step 142. The order information includes but is not limited to an order detail for a medication order, patient demographic information, and other hospital information systems data such as lab results data. The caching mechanism 20 transmits the task list to the input device 32 at step 143.

With reference to FIGS. 4, 5 and 10-11, the input device 32 then displays a task list screen 143A (FIG. 10) which prompts the caregiver 114 to accesses the task list on the input device 32. The input device 32 prompts the caregiver 114 to enter drug specific identification information (dispense ID). The caregiver 114 enters a dispense ID such as the drug container specific machine readable indicator 102. The input device 32 enters this dispense ID at step 144. The input device 32 processes the dispense ID to select the correct task from the task list, then displays a task screen 143B (FIG. 11), and transmits a dispense ID to the caching mechanism 20 requesting an order ID at step 146. The caching mechanism 20 transmits a dispense ID to the HIS 18 requesting an order ID at step 148. The HIS 18 transmits an order ID to the caching mechanism 20 at step 150. The caching mechanism 20 forwards this order ID to the input device 32 at step 152.

Alternatively, the three entered IDs (patient ID, dispense ID, and channel ID) are entered in a different specific order or without regard to order. Where the IDs are entered without regard to order, the IDs would be maintained within the MMS 10 and/or caching mechanism 20 as they are entered, so that the IDs can be recalled when needed to complete the medication delivery workflow.

The input device 32 matches the order ID with an item in the task list to ensure a Five Rights check at step 154. The "Five Rights" in this section refer to the "Five Rights of Medical Administration". Alternatively, the Five Rights check is done at the MMU 12 once the MMU 12 receives the order information as well as the patient, dispense, and channel IDs. A description of these "rights" follows. Right patient, is the drug being administered to the correct patient. Right drug, is the correct drug being administered to the patient. Right dose, is the correct dosage of the drug being administered to the patient. Right time, is the drug being administered to the patient at the correct time. Right route, is the drug being administered into the patient by the correct route, in this case intravenously through an IV. Once the order ID and item in the task list are reconciled, the input device 32 sends an order confirmed message to the caching mechanism 20 at step 156. In response, the caching mechanism 20 sends the order detail (medication order prescribed for a patient) of the order information to the input device 32 at step 158.

Figure 11:
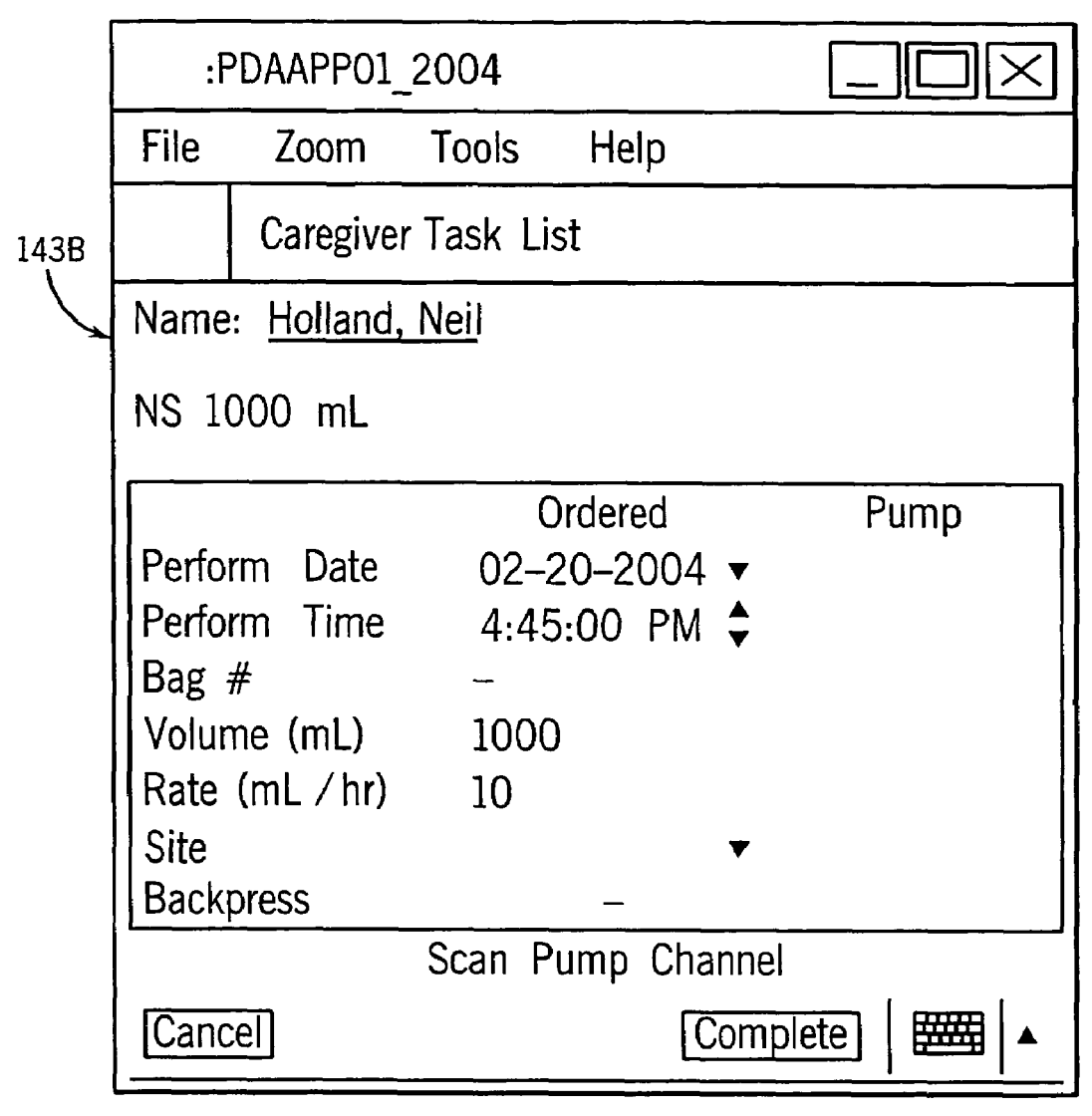

With reference to FIGS. 4, 5, 11, the input device 32 then displays a scan device/channel screen 143B (FIG. 11) which prompts the caregiver 114 to enter channel identification information (channel ID) regarding which channels of the medical device 14 are to be used for the delivery. The caregiver 114 enters a channel ID such as the machine readable indicator 92. The input device 32 enters this channel ID at step 160, and displays a confirmed scan device screen 159B (FIG. 11B) indicating that the channel ID was successfully entered into the input device 32. It will be appreciated that the channel ID indicator 92 can include information also identifying the medical device 14 (medical device ID). Alternatively, it is contemplated that an additional machine readable indicator (not shown) may be provided for the medical device itself separate from the channel ID machine readable indicator 92. If the medical device 14 has a single channel, a single indicator will clearly suffice. If the medical device 14 is a multi-channel device, the channel indicators can also carry information that uniquely identifies the device the channel is on. At any rate, it should be apparent that a second entry of a combined device/channel ID may be redundant and could be eliminated. The input device 32 then transmits the delivery information including caregiver ID, patient ID, medical device ID and/or channel ID, dispense ID, and order ID to the MMU 12 at step 162.

With reference to FIGS. 4, 5 and 12-14, when the medical device 14 is turned on at step 164 the medical device 14 displays a start up screen 163A (FIG. 12) on the display 88 of the medical device 14. The medical device 14 then displays a clinical care area selection screen 163B (FIG. 13) which prompts the caregiver 114 to select the clinical care area (CCA) that the medical device 14 is being assigned to. The caregiver 114 enters or selects the CCA at step 166 using scroll and select/enter keys on the user interface means 86. The medical device 14 then displays a channel selection screen 163C (FIG. 14) that prompts the caregiver 114 to select the desired channel (90 or 94) or bag source (100 or 106 ) using soft keys 163D-G, more particularly 163E, 163F respectively. The medical device 14 enters this channel ID at step 168. The CCA information is transmitted to the MMU 12 by the medical device 14 at step 170. Alternatively, where the CCA is known and available to the HIS 18, the CCA can be automatically generated for the medical device 14, and sent from the HIS 18 to the MMU 12 With reference to FIGS. 2 and 5, the MMU 12 executes the Process Drug Order 46 program and sends an active order request based on the delivery information from the input device 32 to the caching mechanism 20 at step 172. The caching mechanism 20 responds by sending the corresponding patient-specific order information to the MMU 12 at step 174. The caching mechanism 20 may send to the MMU 12 order information regarding all information associated with the particular patient, including but not limited to order detail for a medication order, patient demographic information, and other hospital information systems data such as lab results data or monitoring data.

Referring to FIG. 5A, the MMU 12 then executes the Apply Expert Clinical Rules 50 program to process the CCA information from the medical device 14 and the delivery information from the input device 32, at step 178. The Apply Expert Clinical Rules 50 program compares the delivery information with an expert rule set to determines expert rule set violations based on correlating treatment based protocols, disease based protocols, drug-drug incompatibility, patient data (age, height, weight, etc), vital signs, fluid in/out, blood chemistry, and status assessments (such as pain and cognition). As used herein, the term drug-drug incompatibility includes but is not limited to determinations of drug-drug interactions and/or drug-drug compatibility between two or more medication orders for concurrent delivery (to the same patient at the same time) and/or in a time sequence for the same patient (i.e. through a common output IV line). In cases where the Apply Expert Clinical Rules 50 program finds an expert rule set violation (such as a drug-drug incompatibility), the Apply Expert Clinical Rules 50 program generates an alarm and/or requires a time delay in execution for one of the two separate delivery information submissions.

The Apply Expert Clinical Rules 50 program also establishes a patient-specific rule algorithm. The patient-specific rule algorithm is primarily based on the expert rule set described above applied to a specific order detail. The patient-specific rule algorithm generates a patient-specific rule set (discussed in greater detail below, at the description of FIG. 20) according to patient-specific order information including but not limited to patient demographic information, and other hospital information systems data such as lab results data or monitoring data. The patient-specific rule set includes hard and soft dosage limits for each drug being administered. The patient-specific rule set is included in the delivery programming code sent to the medical device 14 at step 182.

Any alarms generated by the Process Drug Order 46 or Apply Expert Clinical Rules 50 programs are delivered to the medical device 14, HIS 18, and/or input device 32, computer 254 (FIG. 17) at step 180. Computer 254 can be located in a remote nurse station or a biomedical technician area. If no alarms are generated, the MMU 12 transmits a delivery program code to the medical device 14, at step 182. The delivery program code sent from MMU 12 to the medical device 14 includes a patient-specific rule set generated from any rule based adjudication at the MMU 12, including hard and soft dosage limits for each drug being administered. The medical device 14 caches the patient-specific rule set contained in the delivery programcode. Alternatively, the MMU 12 can generate an alarm at the medical device 14 or another location and not download the deliveryprogram code.

Figure 15:
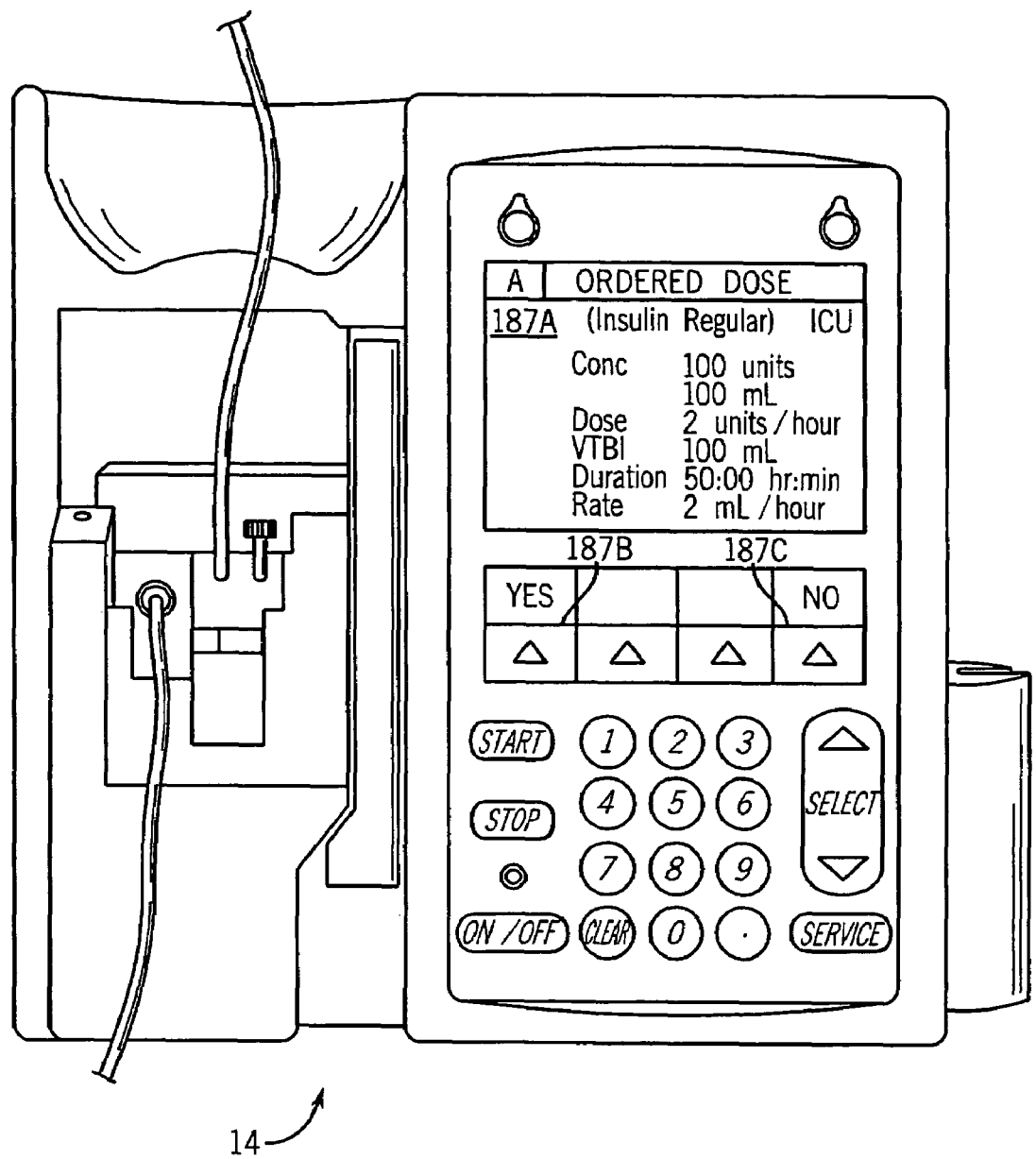
FIG. 15 is a front view of a medical device with a display and user interface means for confirming correct delivery programming code data at the medical device.

With reference to FIGS. 5, 5A and 15, the medical device 14 displays an order dose confirmation screen 187A (FIG. 15) which prompts the caregiver 114 to confirm the delivery data. As shown, the caregiver 114 selects the "yes" soft key 187B on the medical device 14 to confirm the delivery data and the "no" soft key 187C to cancel the delivery. The caregiver 114 confirms the delivery data at the medical device 14 at step 188. Once the caregiver 114 confirms the delivery data at the medical device 14, the medical device 14 then executes the delivery program code and begins infusion at step 198. As part of the program code, the infusion may be delayed for a predetermined period of time.

Alternatively, confirmation from the caregiver can be made at the input device 32 or required from both the input device 32 and medical device 14. As shown, a redundant additional confirmation performed by the caregiver 114 at the input device 32 after the medical device has received the delivery program code. Specifically, the medical device 14 transmits a canonical representation of the delivery programming code data (delivery data) to the MMU 12 detailing the infusion to be performed by the medical device 14, at step 184. The MMU 12 then transmits the same delivery data that was originally transmitted to the medical device 14 to the input device 32 at step 186. Alternatively, the delivery data can be passed to another remote computer (254 in FIG. 17), including but not limited to a computer at a nurse station, for confirmation.

Figure 16:
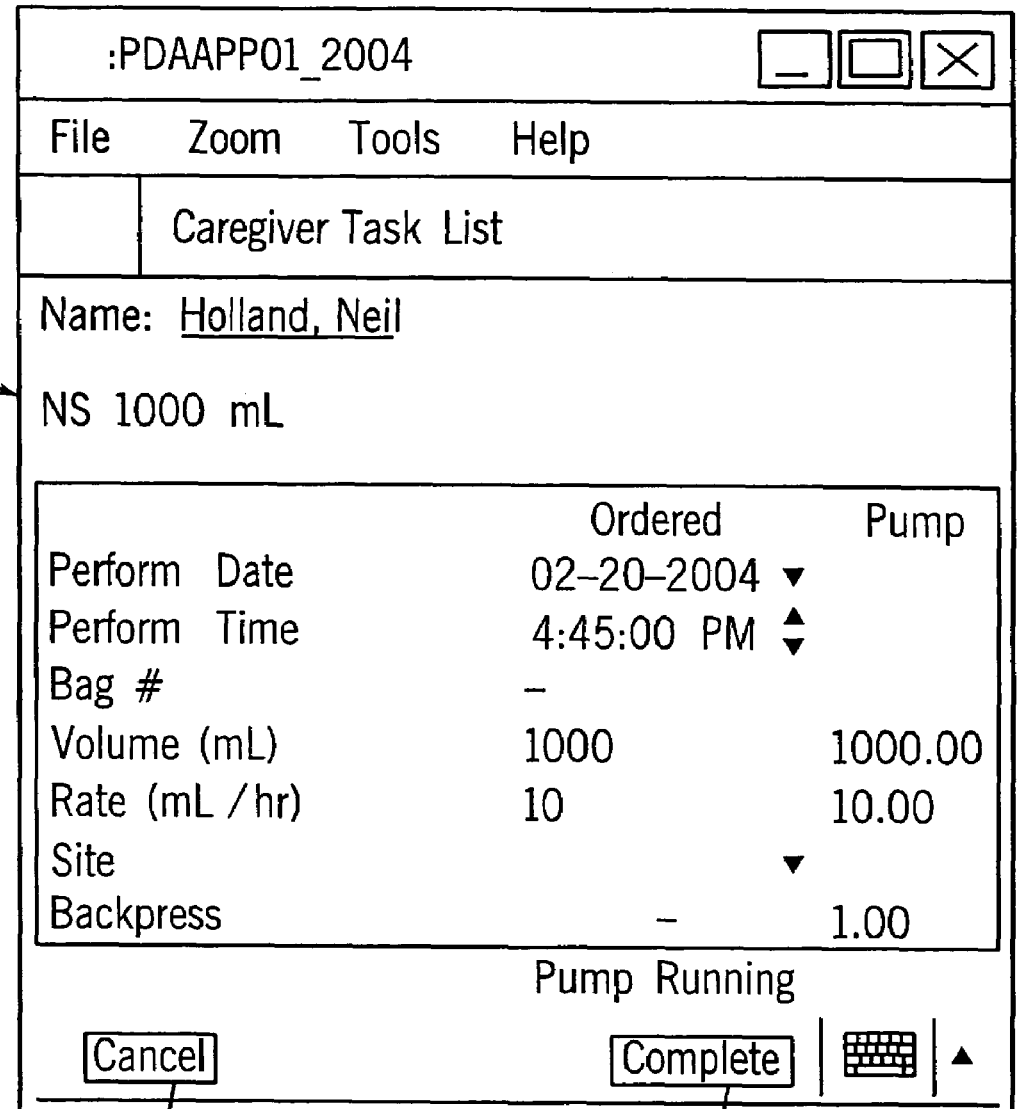
FIG. 16 is a screen shot of a delivery information input device for confirming correct delivery programming code data.

With reference to FIGS. 5A and 16, the input device 32 displays an order dose confirmation screen 191A (FIG. 16) that prompts the caregiver 114 to confirm the delivery data. As shown, the caregiver 114 selects the complete button 191B on the input device 32 to confirm the delivery data and the cancel button 191C to cancel the delivery. The caregiver 114 confirms the delivery data at the input device 32 at step 192, and the confirmation is used for documentation by the HIS 18, or other systems within the hospital environment 16.

With reference to FIGS. 4A and 5A, during infusion, the medical device 14 executes its Process Drug Order 128 program. The Process Drug Order 128 program sends infusion change events and infusion time events in a delivery event log message 200 to the MMU 12. The MMU 12 forwards these delivery event log messages to the input device 32 or other system within the hospital environment 16 at step 202. The caregiver 114 acknowledges these delivery event log messages on the input device 32, at step 204. The input device 32 then sends an acknowledged delivery event log message 206 to the caching mechanism 20, detailing the delivery event, the caregiver ID, and the caregiver acknowledgment. The caching mechanism passes the delivery event message to the HIS 18 at step 208.

Once infusion has ended at step 210, the medical device 14 sends an infusion ended message 212 to the MMU 12. The MMU 12 then aggregates all the delivery event messages 200 sent during the infusion at step 214. The MMU 12 sends the aggregated delivery events 216 to the input device 32. The caregiver 114 enters a completed task 218 on the input device 32, and sends the aggregated delivery events to the caching mechanism at step 220, which in turn passes the delivery event log messages to the HIS 18 at step 222.

Figure 6:
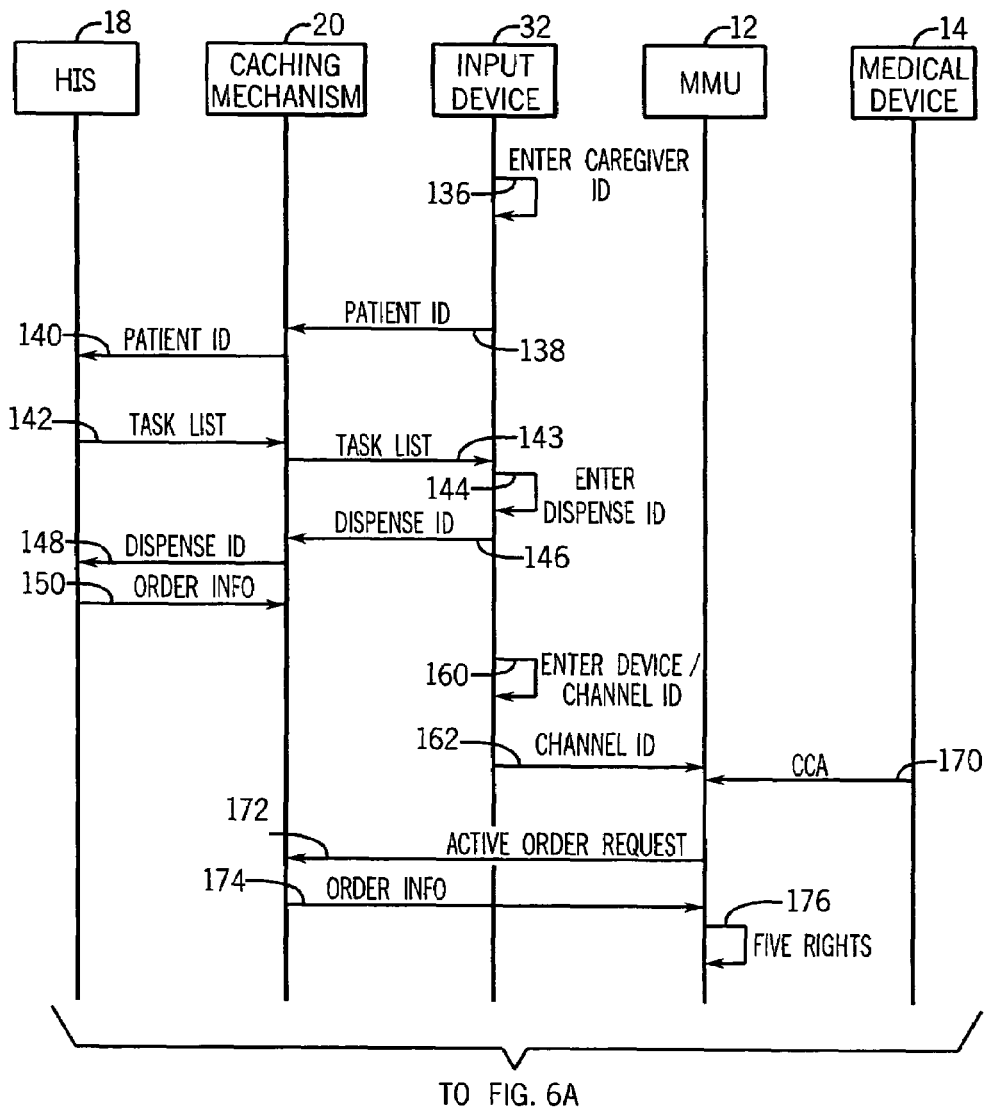
FIG. 6, is an alternative flow chart of the medication management system processing a drug order through the medication management unit and medical device, and integrated with an information system according to the invention.
Figure 6A:
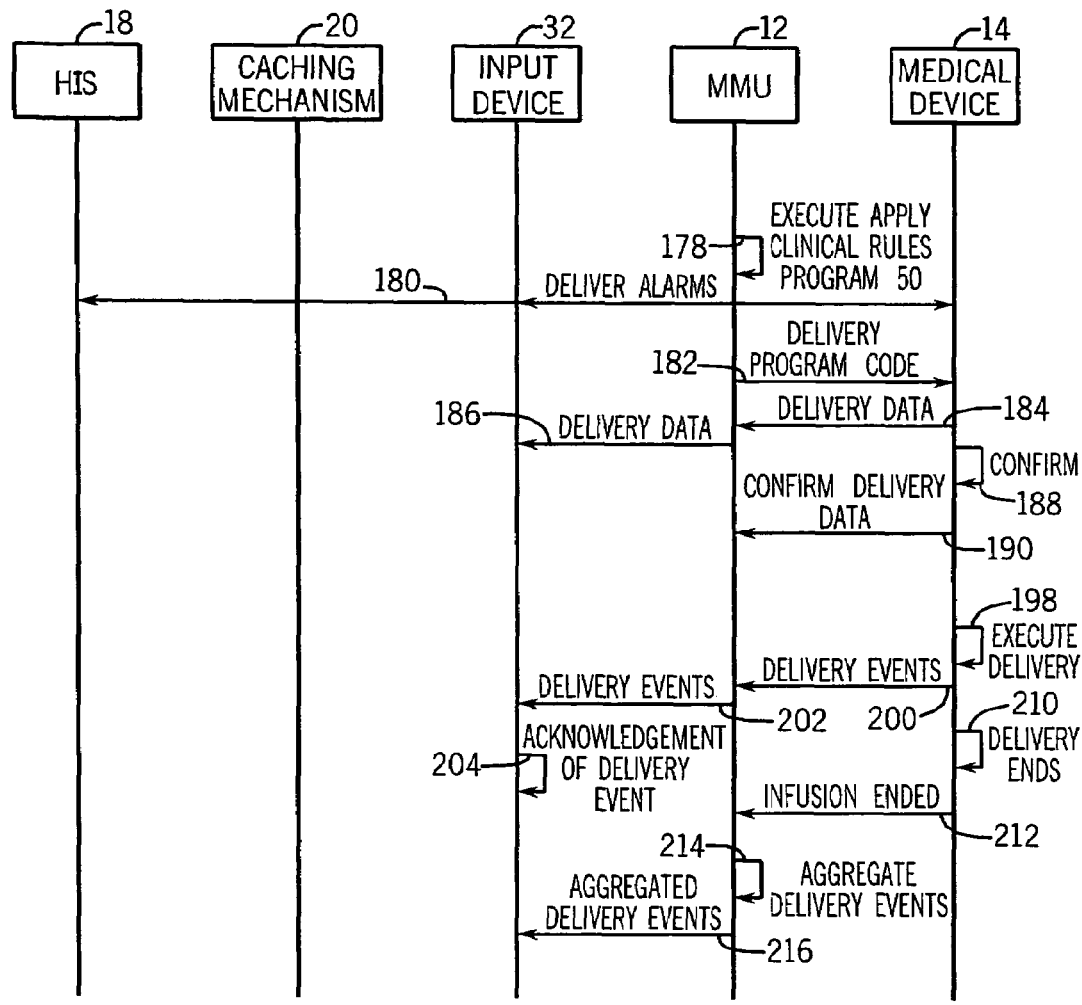
FIG. 6A is a continuation of the flow chart of FIG. 6.

With reference to FIG. 6 and 6A, an alternative flow chart of the MMS 10 processing a drug order through the MMU 12 and medical device 14 is shown. With reference to FIGS. 4, 6 and 6A, the caregiver 114 enters the patient ID, which then is stored in the caching mechanism 20. The caching mechanism 20 transmits the patient ID to the HIS 18 and retrieves a patient-specific task list for that patient ID. The caregiver 114 then enters the dispense ID, which subsequently is stored in the caching mechanism 20. The caching mechanism 20 transmits the dispense ID to the HIS 18, and retrieves a patient-specific order information, including but not limited to an order detail, patient demographic information, and other hospital information systems data such as lab results data. The caregiver 114 then enters the channel ID, which is stored in the MMU 12.

Alternatively, the three entered IDs (patient ID, dispense ID, and channel ID) are entered in a different specific order or without regard to order. Where the IDs are entered without regard to order, the IDs would be maintained within the MMS 10 and or caching mechanism 20 as they are entered, so that the IDs can be recalled when needed to complete the medication delivery workflow.

Upon receipt of the channel ID, the MMU 12 requests the order information (order detail, patient demographic information, and other hospital information systems data) and retrieves it from the caching mechanism 20. This order information is stored within the MMU 12 and utilized for subsequent rule processing such as "Five Rights" checking and other rule set algorithms. The Process Drug Order 46 program processes the delivery information from the input device 32 (including caregiver ID, patient ID, medical device/channel ID, and dispense ID) and compares this delivery information with the corresponding order detail portion of the order information from the caching mechanism 20, at step 176. Where the order information and delivery information do not match, the device program code downloaded to the medical device 14 at step 182 includes an alarm message indicating that the five rights check was not met. Additionally, the alarm message can include a description of which particular right(s) did not match. Alternatively, the NMU 12 can generate an alarm at the medical device 14 or another location and not download the program code for delivery of the medication order.

Alternatively, the MMU 12 can accept a Five Rights check from another device, such as a HIS 18 or an input device 32. This check can be accepted either by a direct data element being sent to the MMU 12 indicating a Five Rights check, or implied through the workflow provided by the HIS 18 or input device 32.

The other steps shown in FIGS. 6 and 6A are similar to corresponding steps in FIGS. 5 and 5A. Accordingly, these steps will not be described with any further detail here. One skilled in the art will appreciate that the vertical lines in FIGS. 5, 5A, 6, 6A do not necessarily represent a firm time sequence. Some steps may be done sooner than shown (for example, turning on the medical device) or later than shown (for example, aggregate delivery events).

With reference to FIGS. 2, 4A, 5, 5A and 20, in one embodiment, the Process Drug Order 46 program of the MMU 12 and the corresponding Process Drug Order 128 program of the medical device 14 permit the MMU 12 to remotely control the medical device 14 to modulate performance of a medication order. For example, the MMU 12 can remotely start and/or stop the medical device 14. Once the delivery program code is received by the medical device 14 at step 184, the Process Drug Order 46 of MMU 12 remotely starts execution of the infusion by sending a start order 224, which triggers the medical device to begin infusion at step 225. Likewise, when the infusion is to end at step 228, the Process Drug Order 46 program can remotely stop the infusion by sending a stop order 226 to the medical device 14, which triggers the medical device to end infusion at step 228. In most cases, the MMU 12 requires the caregiver to confirm the start or stop of execution. This confirmation by the caregiver may take place at the input device 32 or the medical device 14. However, one skilled in the art will appreciate that there may be emergency situations where an order could and should be stopped without human confirmation.

With reference to FIGS. 2, 5, 5A and 20, in one embodiment, the Apply Expert Clinical Rules 50 program of the MMU 12 permits the MMU 12 to adjust a previously fixed patient-specific rule set based on new patient conditions and/or recent lab results, and notify the caregiver that adjustment is recommended by the MMU 12. As discussed above in regard to FIGS. 5 and 5A, the Apply Expert Clinical Rules 50 program establishes a patient-specific rule algorithm. The patient-specific rule algorithm is primarily based on the expert rule set described above applied to a specific order detail. The patient-specific rule algorithm generates a patient-specific rule set according to patient-specific order information including but not limited to patient demographic information, and other hospital information systems data such as lab results data or monitoring data. The patient-specific rule set includes hard and soft dosage limits for each drug being administered, and these hard and soft dosage limits likewise are adjusted when the patient-specific rule set is adjusted.

Figure 20:
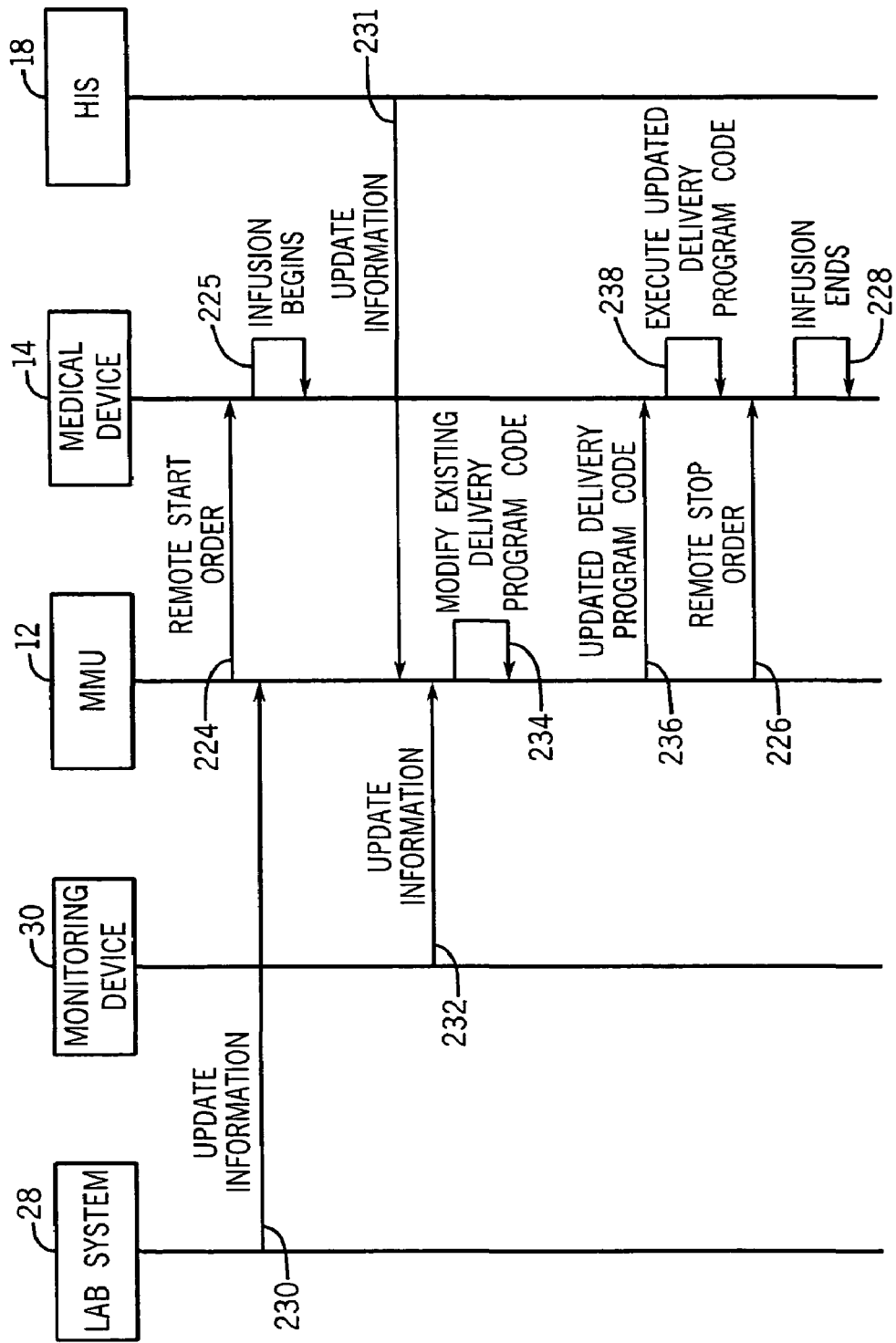
FIG. 20 is a flow chart of the medication management system updating a delivery program code executed on the medical device based on new information from a lab system, HIS and/or monitoring device.

For example, during or even before an infusion, the MMU 12 may receive updated patient information that can impact an ongoing or impending infusion. As shown in FIG. 20, the lab 28 sends updated patient-specific lab results to the MMU 12 at step 230. Likewise, the monitoring device 30 sends updated patient-specific monitoring information to the MMU 12 at step 232. Additionally the MMU 12 queries the HIS 18 for patient information including: Patient Allergies, Patient Diet, and Current Patient Medical Orders. Patient Allergies are used to check for drug-allergy interactions, at step 231. Patient Diet information is used to check for drug-food interactions. Current Patient Medical Orders are used to check for drug-drug incompatibility. Like the patient information gathered from the Lab 28 and the monitoring device 30, the patient information from HIS 18 is also used by the MMU 12 to update the delivery program order.

As shown in FIGS. 5 and 5A, in cases where the MMU 12 is processing a drug order for the medical device 14, the MMU 12 executes the Apply Expert Clinical Rules 50 program at step 178 to establish a patient-specific rule set based on updated patient information received or retrieved from the lab 28, the monitoring device 30, and or the HIS 18 (FIG. 20). This real-time or near delivery time updated patient-specific information is useful in adapting patient therapy because it may not have been available at the time the medication order was prescribed.

As shown in FIG. 20, The MMU 12 also modifies the existing patient-specific rule set in the existing delivery program code at step 234 based on updated patient information received or retrieved from the lab 28, the monitoring device 30, and or the HIS 18. The MMU 12 optionally alerts the input device 32 and/or the medical device 14 of changes to the patient-specific rule set. MMU 12 also optionally generates an alert message if the delivery programming code violates any parameter of the adjusted hard and soft dosage limits. Additionally, the MMU 12 optionally requests confirmation by the caregiver prior to instituting the new patient-specific rule set. The MMU 12 then delivers an updated delivery program code to the medical device 14 for execution at step 236. The medical device 14 then executes this updated delivery program code as step 238. The updated delivery program code sent from MMU 12 to the medical device 14 includes an updated patient-specific rule set generated from any rule based adjudication at the MMU 12, including hard and soft dosage limits for each drug being administered. The medical device 14 caches the updated patient-specific rule set contained in the delivery program code. Additionally, the MMU 12 collects, stores, and reports the changes to the patient-specific rule set, changes to the hard and soft limits, as well as the history of each medication order.

An example of how the MMU 12 updates the patient-specific rule set based on lab results or monitored patient conditions is provided below with respect to the drug Heparin, which is a blood thinner. The medication order entered by the physician might be:

Give heparin 1000 units/hour. If the activated partial thromboplastin time (APTT)>75 seconds then decrease heparin to 800 units/hour.

If the medical device 14 has started the infusion at 1000 units/hour and the MMU 12 subsequently receives an updated APTT value of 100 seconds from the lab 28 on the patient, the MMU automatically commands the medical device 14 to decrease the infusion rate to 800 units/hour. Alternatively, when the MMU is notified by lab 28, an alarm will be generated to the PDA 32 and/or the medical device 14 to notify the caregiver of the need to change the infusion rate. The MMU can preprogram the pump for the caregiver to confirm the recommended change.

In further embodiment or method, the hospital may establish expert rules or clinical decision support rules in the MMU 12 that will be applied automatically to incoming prescribed orders, such that the physician may simply write an order for 1000 or 1200 units/hour. The hospital best practices formulated by the appropriate medical personnel are established in the MMU 12 and can dictate that all heparin orders are to be conditioned on the APTT lab result and such an expert rule or clinical decision support rule will be used by the MMU 12 to govern the operation of the medical device 14. The MMU 12 also can check the most recent patient data and provide an alarm and/or temporarily modify the delivery order prior to the start of the infusion if the prescribed order is no longer appropriate given the expert rules or clinical decision support rules and the latest lab results or monitored patient conditions. It should be apparent that this kind of intervention by the MMU 12 during or immediately prior to an infusion is particularly useful in preventing adverse consequences for the patient and the hospital.

Where the MMU 12 adjusts a previously fixed patient-specific rule set based on new patient conditions and/or recent lab results, as described above, the MMU 12 provides dynamic advanced reports of real-time rule set changes in relation to changes in the condition of the patient (an "information cascade"). These advanced reports detail the history of both hard and soft upper and lower limits, as well as the activation of overrides and confirmations based on these limits for each medical device 14 managed by the MMU 12. Further details on this feature can be found in commonly owned co-pending application entitled SYSTEM FOR MAINTAINING DRUG INFORMATION AND COMMUNICATING WITH MEDICATION DELIVERY DEVICES filed on Feb. 20, 2004, which is expressly incorporated herein in its entirety.

Figure 19:
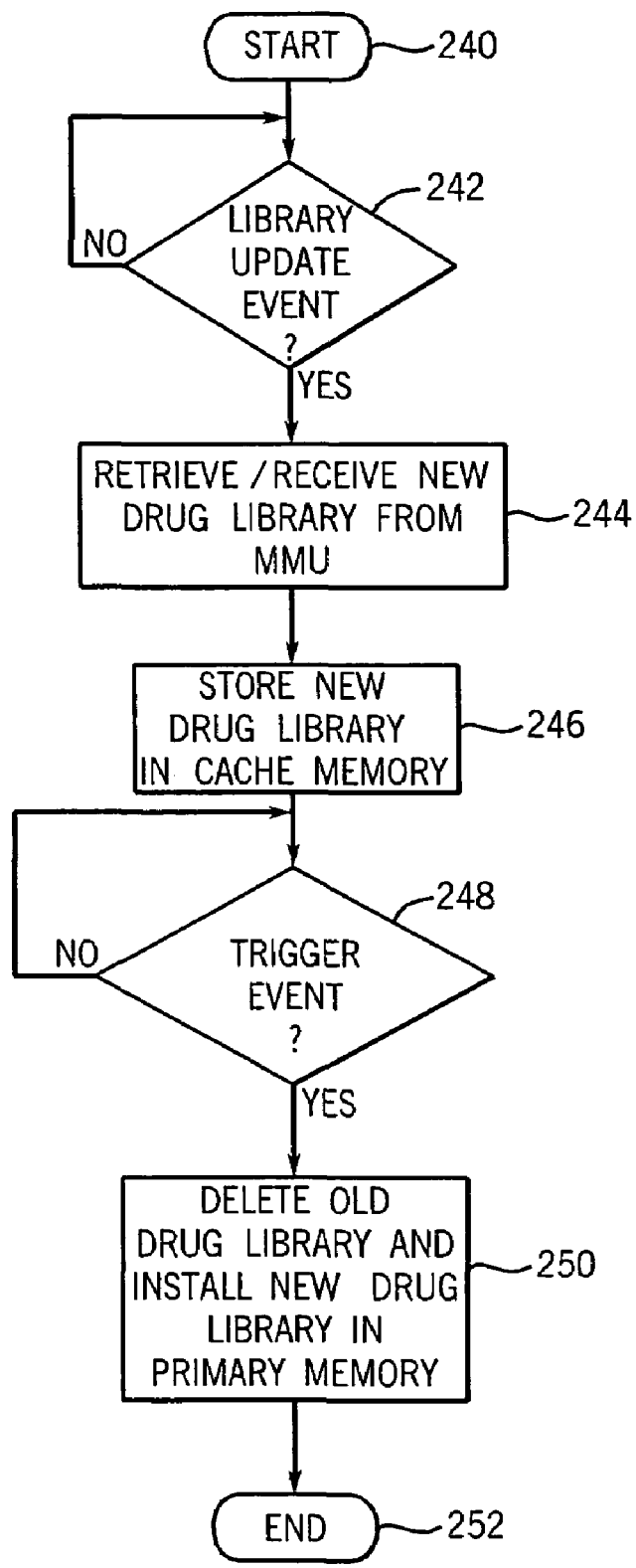
FIG. 19 is a flow chart of the medical device retrieving/receiving an updated drug library from the medication management unit.

With reference to FIGS. 2, 4A and 19, the Download Drug Library 44 program in the MMU 12 and the corresponding Download Drug Library 132 program in the medical device 14 operate to send a drug library to the medical device 14 from the MMU 12. The drug library includes drug and device related information, which may include but is not limited to drug name, drug class, drug concentration, drug amount, drug units, diluent amount, diluent units, dosing units, delivery dose or rate, medication parameters or limits, device/infuser settings and/or modes, CCA designations and constraints, and library version. The Download Drug Library 132 program is designed to cache in a cache memory 126A a new database or drug library at medical device 14 while maintaining an existing older version database or drug library in its primary memory 126. This allows the medical device to operate or deliver an infusion based on the older version of the drug library without disruption until a trigger event occurs, at which time the new drug library replaces the older version in the primary memory 126. It is contemplated that the medical device 14 can be equipped with an initial drug library at the factory.

The Download Drug Library 132 program in the medical device 14 begins at a block 240 and at block 242 a determination is made that a drug library update needed event has occurred. For instance the drug library update needed event could be a completed infusion, a stopped infusion, elapsed time, a specific date and time, creation of the new drug library, the medical device 14 being or entering into a particular configurable mode such as stop, "sleep" or "wakeup", connection of the medical device 14 to an access node 84 in a new CCA, a download of a new or modified drug library to the medication management unit, or a determination that the existing drug library at the medical device needs updating. The configurable mode could be any number of device modes including a power-on sleeping mode and a power-off mode. The determination that a drug library update needed event has occurred can be made by (at) the MMU 12, the medical device 14 or by a combination of the two.

Based on the specific drug library update needed event, the Download Drug Library 132 proceeds to block 244 where it retrieves or receives a new drug library. Once retrieved or received, the Download Drug Library 132 proceeds to block 246 where it stores the new drug library in the cache memory 126A of the medical device 14. While a medical device 14 is operating on a patient or in an otherwise nonconfigurable mode, information such as a new drug library or database is stored in a cache memory 126A of the medical device 14 as the information is received from a wired or wireless link through the network interface 122. The Download Drug Library 132 proceeds to block 248 where it determines if a specific trigger event has occurred. For instance, the trigger event could be a completed infusion, a stopped infusion, a determination that the device is in a configurable mode, elapsed time, a specific date and time, creation of the new drug library, a download of a new or modified drug library to the medication management unit, and a determination that the existing drug library at the medical device needs updating. The configurable mode could be any number of device modes including a power-on sleeping mode and a power-off mode. The determination that a trigger event has occurred can be made by (at) the MMU 12, the medical device 14 or by a combination of the two.

The Download Drug Library 132 then proceeds to block 250 where it deletes the existing drug library in primary memory 126 and installs the new drug library, and the new drug library from cache memory 126A will replace the older information in the memory 126 of the medical device 14. The Download Drug Library 132 process is then complete and ends in block 252.

Additional related features of the Download Drug Library 44 program in the MMU 12 and the corresponding Download Drug Library 132 program include recording the history of the download, verify the correct download, notification to the caregiver of a change of library, and a preliminary note on the medical device 14 display stating that the drug library will be changed after any current infusion (i.e., before the next infusion).

Additionally, partial updates of the drug database within the medical device 14 are also made possible by the present invention. The MMU 12 is supplied with a drug database that allows a user to update a single data item (row, column, or cell) in the database without re-writing the entire database. This provides faster processing and downloading times when modifying the drug database.

Further, the Download Drug Library 44 program in the MMU 12 is designed to modify a medication library from the HIS 18 in such a way that only a single configuration of a single drug library is necessary to provide download information to multiple separate and different medical devices 14 where each device has unique parameters (different models, processors, computer architecture, software, binary format, or manufacturers, for example). In this embodiment, the configured drug library is designed so that only a subset of the configured drug library is specific for each unique type of medical device 14, and only the specific information is selected for transfer to each medical device 14. Additionally, pre-validation of the configured drug library is done through use of a rule set editor prior to sending from the MMU 12 to the medical device 14, and post-validation occurs where the medical device 14 confirms receipt of an acceptable drug library back to the MMU 12. Further details on these additional related features can be found in commonly owned co-pending application entitled SYSTEM FOR MAINTAINING DRUG INFORMATION AND COMMUNICATING WITH MEDICATION DELIVERY DEVICES filed on Feb. 20, 2004, which is expressly incorporated herein in its entirety.

With reference to FIGS. 2, 3, and 4A, the Monitor Pump 44 program in the MMU 12 and the corresponding Monitor Pump 130 program in the medical device 14 operate to map the approximate or general physical location of each medical device 14 within the hospital environment and to enable a user to trigger a locator alarm to locate a particular medical device 14. Additionally, the programming enabling the medical device locator would be located in an asset manager 64 portion of the MMU 12.

Figure 17:
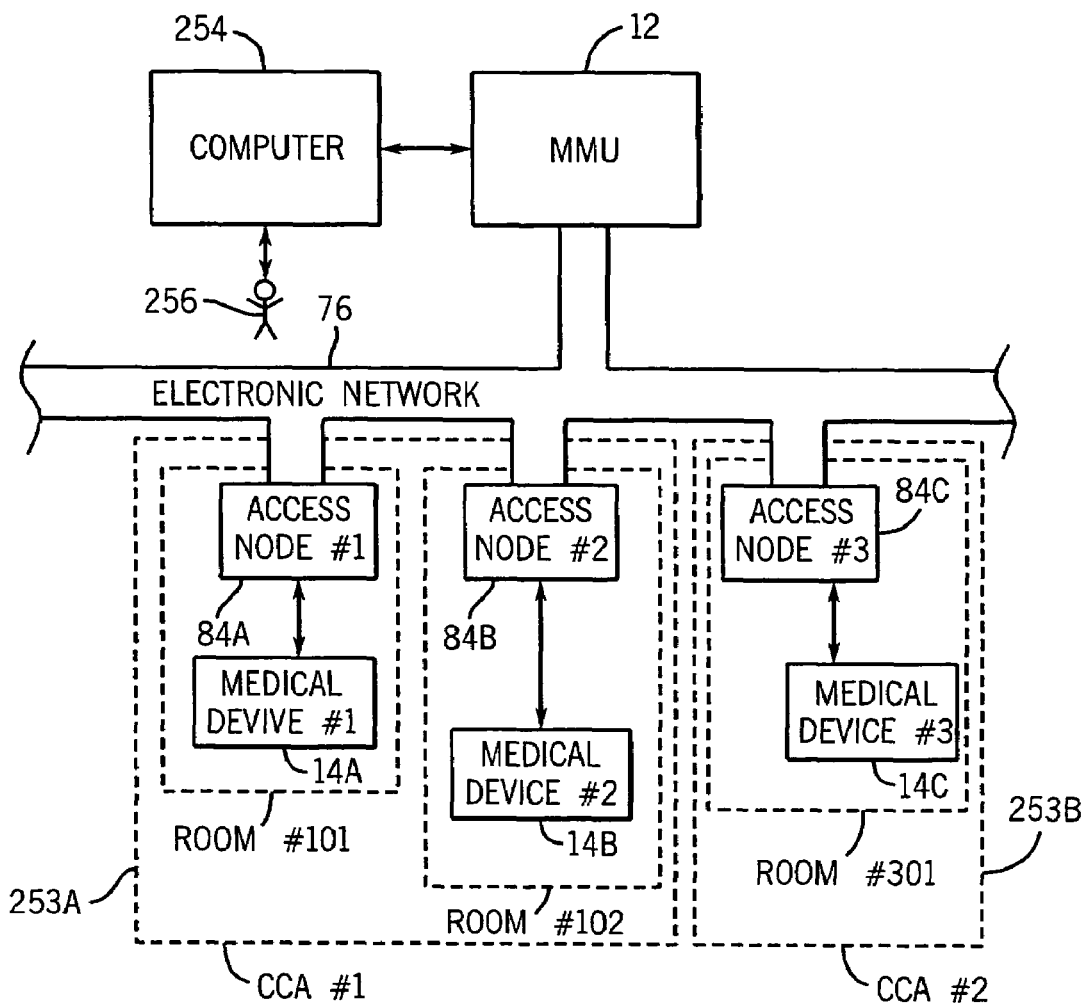
FIG. 17 is a schematic diagram of the medication management system including a medication management unit and one or more medical devices, showing the medication management unit communicates with a medical device to locate the device.

With reference to FIG. 17, the MMU 12 communicates with one or more (more preferably a plurality of) medical devices 14A, 14B, and 14C through the electronic network 76. The medical device or devices 14A, 14B, and 14C connect to the electronic network 76 through one or more (more preferably a plurality of) access nodes 84A, 84B, and 84C distributed in one or more (more preferably a plurality of) CCAs 253A and 253B. More than one medical device 14 can operate from an individual access node 84 and be associated with a particular patient. Typically, there is one access node per room (101, 103, and 301), but it also is possible to have more than one access node per room and more than one room or CCA per access node. Additionally, as discussed above with regard to FIG. 4, the connection between the medical devices 14A, 14B, and 14C and the access nodes 84A, 84B, and 84C can be wireless. A user access device such as a computer system 254 is remotely located from the MMU 12 and the medical device 14 and communicates with the MMU 12 to permit a user 256 to activate the Monitor Pump 44 program in the MMU 12 and remotely activate the corresponding Monitor Pump 130 program in the medical device 14. The computer 254 can be located in a variety of locations, including but not limited to a nurse station or a biomemdical technician area.

Figure 18:
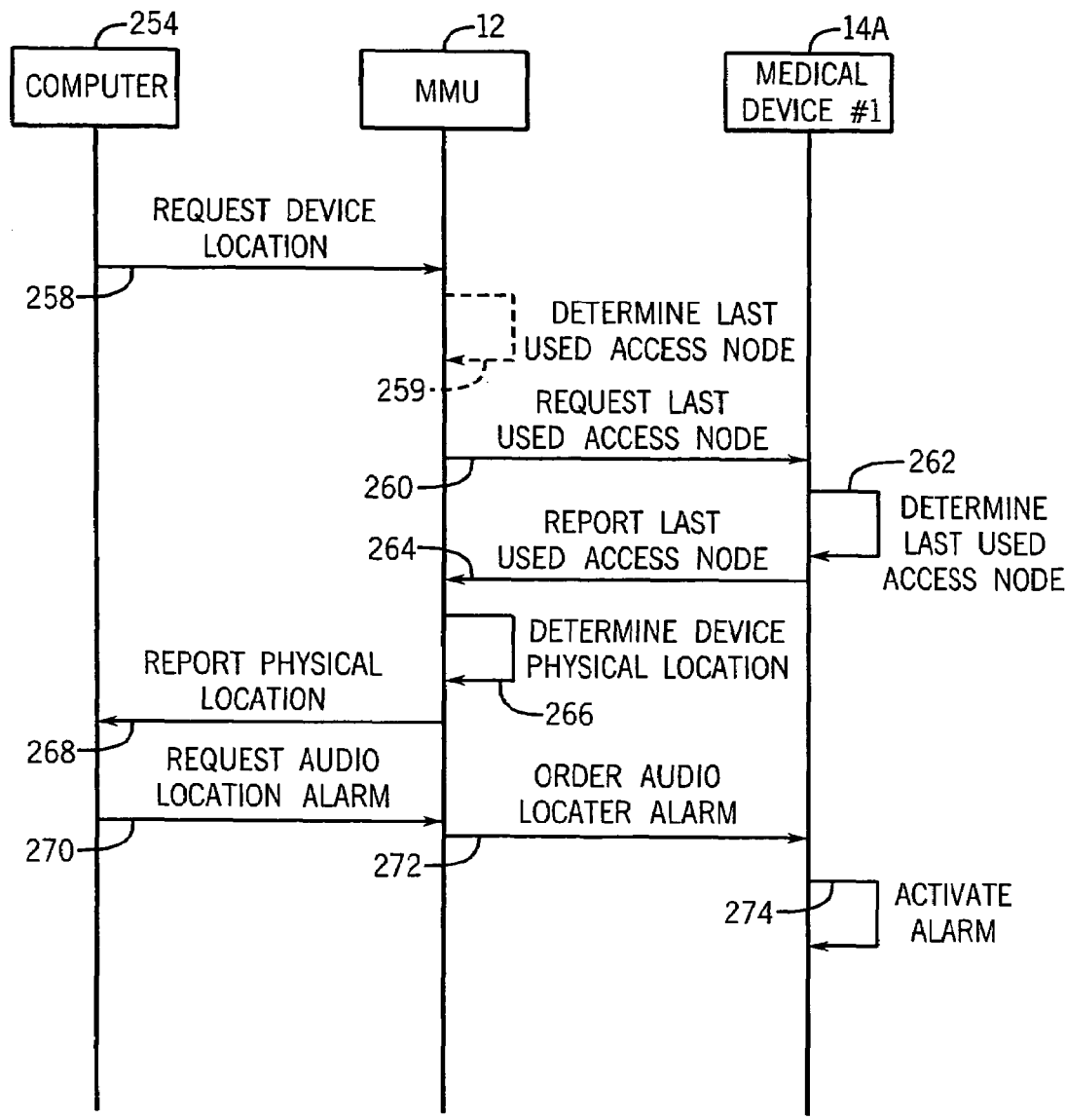
FIG. 18 is a flow chart of the medication management system locating a medical device.

With reference to FIG. 18, the functional steps of the Monitor Pump 52 program in the MMU 12 and the corresponding Monitor Pump 130 program in the medical device 14A are shown in operation with the computer 254. To begin to request a physical location for a medical device 14, the user 256 (not shown) enters a query for the location of a medical device 14A. The computer 254 sends a request device location 258 message to the MMU 12. The MMU 12 in turn sends a request last used access node 260 message to the medical device 14A. It is also contemplated that the Monitor Pump Program 130 can be operated with the input device 32.

The medical device 14A determines the last access node 84A-84C used to connect with the electronic network 76 at step 262. A report of the last used access node 264 is sent from the medical device 14 to the MMU 12. The MMU 12 processes the report of the last used access node 264 to determine the general physical location of the device at step 266. Once the physical location of the medical device 14A is determined by the MMU 12, a report physical location 268 message is sent from the MMU 12 to the computer 254. Additionally, the MMU 12 tracks "change of infuser access node" events, when a medical device 14 begins to communicate through a different network access node 84. The MMU 12 communicates the physical locations of medical devices 14 to the HIS 18.

If the user 256 requires additional assistance in locating the particular medical device 14A, the user 256 can instruct the computer 254 to send a request audio location alarm 270 message to the MMU 12. The MMU 12 in turn sends an order audio locator alarm 272 message to the medical device 14A. The medical device 14A then activates an audio alarm at step 274 to assist the user 256 in locating the medical device 14A. The audio alarm activation can be delayed by a predetermined time to allow the user time to travel to the area of the last used access node. The audio alarm feature is useful in allowing the user to more precisely pinpoint the location of the medical device 14. The audio alarm feature is particularly useful if the medical device 14 is very close to other medical devices or has been moved to a storage closet or other location where it is not readily apparent visually.

Alternatively, the functional steps of the Monitor Pump 44 program in the MMU 12 and the corresponding the Monitor Pump 130 program shown in FIG. 18 can be performed as a series of "push" steps instead of a series of "pull" steps (as shown in FIG. 18). In a "push" embodiment the medical device 14A periodically determines the last used access node and periodically reports the last used access node to the MMU 12 as a "here I am" signal. Likewise, the MMU 12 periodically determines the physical location of the medical device 14A based on the last access node 84A used by the medical device 14, and periodically reports the physical location of the medical device 14A to the user access device 254. Alternatively, the MMU 12 programming allows it to determine which of access nodes 84 was the last access node used by the device 14 (step 259 indicated by a dashed line) and the MMU can report the general physical location of the medical device 14 to the computer 254 without requesting a report from the medical device 14.

Figure 21:
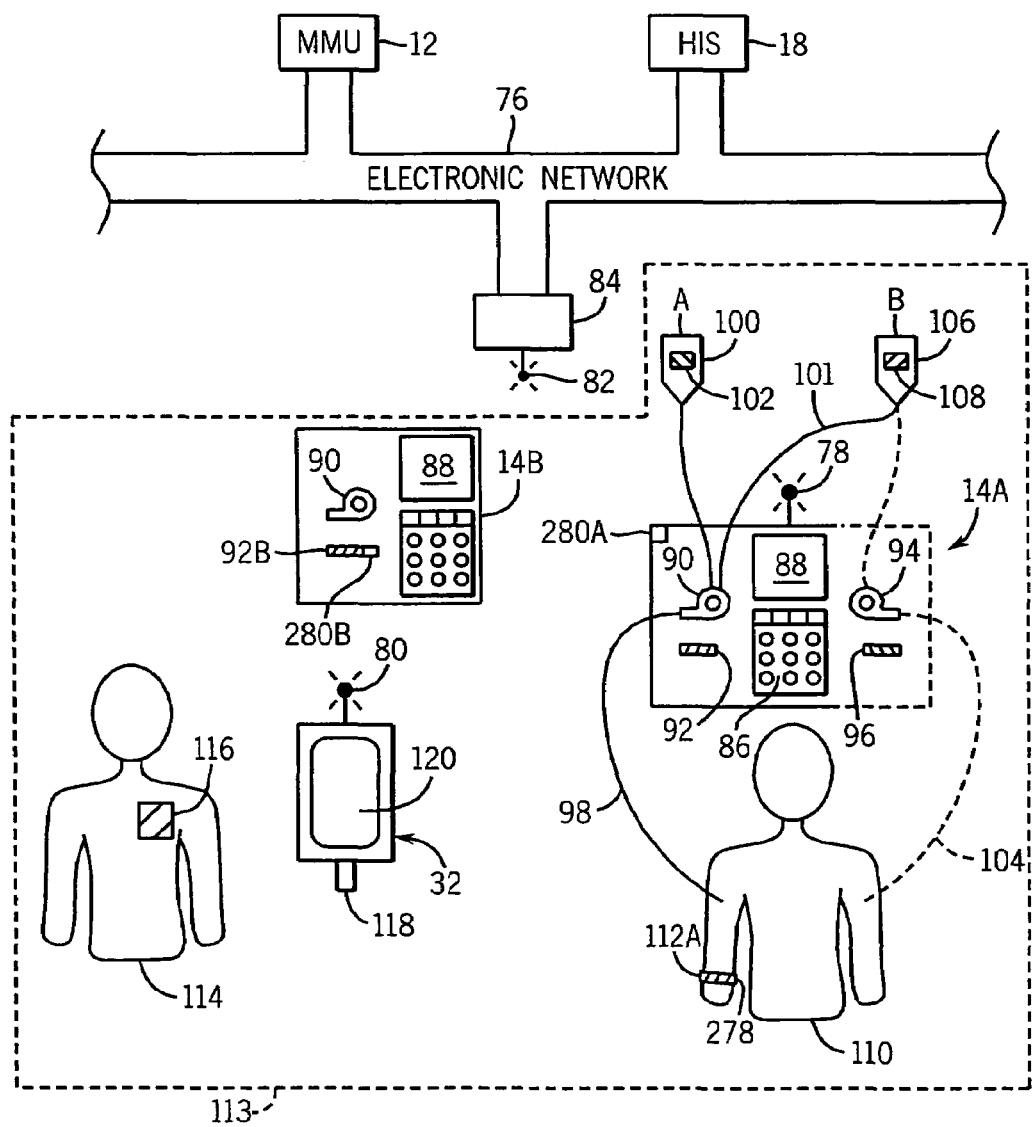
FIG. 21 is an alternative pictorial schematic diagram of the medication management system and its interaction with medical devices and the information system.

In one embodiment described above, the association between medical devices 14, patient 110, drug 100, and caregiver 114 (if present), is accomplished by swiping machine readable indicators on each of these elements of the PAN 113 (See FIG. 4). This association is made in software residing the MMU 12. Alternatively, the association is made in software residing in the medical device 14. With reference to FIG. 21, in another embodiment, the association between medical devices 14A, patient 110, drug 100, and caregiver 114, is accomplished by "auto-association". Auto-association is desirable in situations where the patient's wrist is not readily accessible (e.g. during surgery, or a neonate in an incubator).

In the auto-association embodiment, the MMU 12 and medical device 14A are designed to establish the patient as the focus of the MMS 10. In this embodiment, the patient 110 is equipped with a machine readable indicator 112A on a wristband, toe tag, badge or similar article. The machine readable indicator 112A contains transmitter/receiver chip 278, capable of short-range transmission. The transmitter/receiver chip 278 is a low power RF Bluetooth™, a dedicated RF transmitter working with a PIC processor, or any other suitable transmitter/receiver. The patient 110 is fitted with the machine readable indicator 112A at the time of admission. The unique ID number of the particular machine readable indicator 112A is stored with an electronic patient record at the HIS 18 and hence MMU 12. The MMU 12 is thereby notified of the particular machine readable indicator 112A associated with the particular patient 110. Additionally, it is contemplated, that any other machine readable indicator used with the present invention, may also contains transmitter/receiver chip capable of short-range transmission. For instance, the caregiver machine readable indicator 116 and medication machine readable indicator 102 may also be equipped with a transmitter/receiver chip.

Each medical device 14A is also equipped with a transmitter/receiver chip 280A. Upon placing a medical device 14 at the patient 110 bedside, within the PAN 113, the transmitter/receiver chip 280A of the medical device 14A "pings" by sending out a "request for patient" command to any transmitter/receiver chip 278 that is in the area. Each transmitter/receiver chip 278, which is in the area (usually about 0-10 meters, more preferably about 0-3 meters), replies to the ping by sending the transmitter/receiver chip 280 of the medical device 14A the unique ID number of the particular machine readable indicator 112A. Upon receipt of a signal from the machine readable indicator 112A, the medical device 14A places the ID number of the machine readable indicator 112A in memory 126 (See FIG. 4A) and also transmits the same to the MMU 12. Alternatively, the unique ID of the indicator 112A can be transmitted directly to an MMU 12 located in the area or indirectly through another route, including but not limited to the medical device 14. With reference to FIGS. 5, 5A, 6 and 6A, the MMU 12 Process Drug Order 46 program then checks the patient ID entered at step 162 and the device/channel ID entered at step 160 to ensure the correct match. The MMU 12 associates the medical device 14A only to the identified patient based on the patient ID number sent to the MMU 12. Dissociating the medical device 14A from the patient is done based on a command from a user, or other method.

It should be noted, that the machine readable indicator 112A (as well as the machine readable indicator 112), can include equipment for monitoring the wearer, and transmitting this monitored information to the medical device 14 and/or the MMU 12.

With reference back to FIG. 21, placing a second medical device 14B within the PAN 113 leads to a repeat of the same process. In this case the first medical device 14A "pings" any transmitter/receiver chip that is in the area. The transmitter/receiver chip 280B of the second medical device 14B replies to the ping by sending the transmitter/receiver chip 280A of the first medical device 14A the unique ID number of the particular machine readable indicator 92B. Upon receipt of a signal from the machine readable indicator 92B, the first medical device 14A places the ID number of the machine readable indicator 92B in memory 126 (See FIG. 4A) and also transmits the same to the MMU 12. The patient ID number is then sent from the first medical device 14A to the second medical device 14B.

An additional or alternative validation of the "right patient" can be accomplished by caregiver visual confirmation of the patient following the auto-association procedure described above in relation to FIG. 21, and is also applicable to the five-rights procedures described above with respect to FIGS. 5, 5A, 6 and 6A. In this process, the patient 110 is photographed with a digital camera (not shown) at the time of admission and the digital photo is stored with the electronic patient record at the HIS 18. When a medication order is requested for a specific patient, the digital photo is sent to the MMU 12 and upon completion of the association process, the digital photo is transmitted from MMU 12 to the medical device 14 at the patient 110 bedside. The image of the patient 110 is sent to the display 88 of the medical device 14, which is preferably a high resolution touch screen at least approximately 12 cm by 12 cm. The image of the patient 110 is then placed on the display 88 and the caregiver 114 is prompted by the display 88 to "Confirm Patient". The caregiver 114 confirms a patient match upon visual comparison of the patient 110 with the image on the display 88.

Alternatively, the digital photo information alternatively can be stored on the indicator 112 or 112A and transmitted by the transmitter/receiver 178 thereof. The digital photo is transmitted to the medical device 14 when the medical device 14 has been associated with the patient 110.

Figure 22:
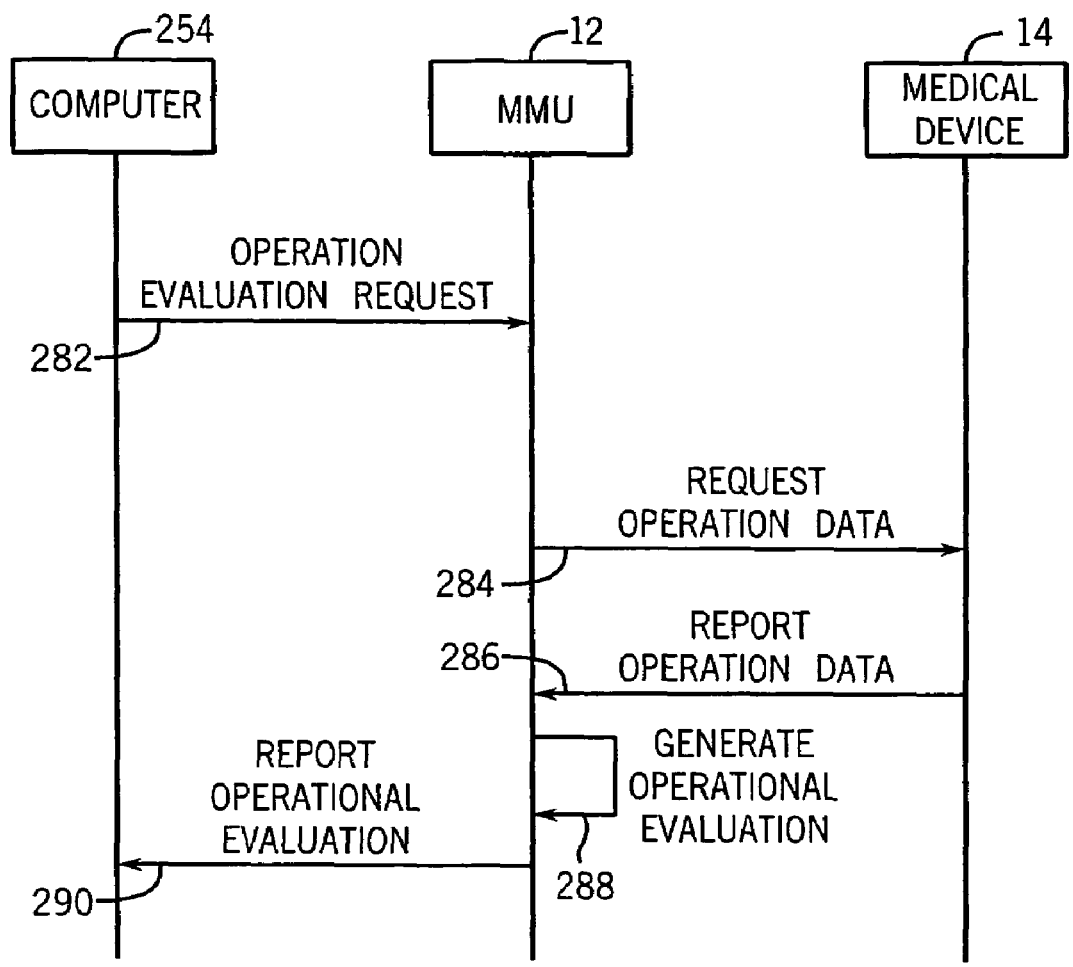
FIG. 22 is a flow chart of the medication management system generating an operation evaluation report of a caregiver or medical device.

With reference to FIG. 22, another portion of the functional steps of the Monitor Pump 52 program in the MMU 12 and the corresponding Monitor Pump 130 program in the medical device 14 are shown in operation with the computer 254. To begin to request a specific evaluation for the operation of a specific medical device 14, or group of medical devices 14, the user 256 (not shown) enters a query for the operation evaluation of a medical device 14. The computer 254 sends an operation evaluation request 282 message to the MMU 12. The MMU 12 in turn sends a request operation data 284 message to the medical device 14. The medical device 14 sends a report operation data 286 message (including but not limited to event logs, settings, CCA and utilization information) back to the MMU 12 at step 286. The MMU 12 processes the report operation data 286 to generate an operational evaluation at step 288. Once the operational evaluation of the medical device 14 is determined by the MMU 12, a report operational evaluation 290 message is sent from the MMU 12 to the computer 254.

Alternatively, the functional steps of the Monitor Pump 44 program in the MMU 12 and the corresponding the Monitor Pump 130 program shown in FIG. 22 can be performed as a series of "push" steps instead of a series of "pull" steps (as shown in FIG. 22). In a "push" embodiment the medical device 14 periodically reports the operation data to the MMU 12. Likewise, the MMU 12 periodically processes the report operation data 286 to generate an operational evaluation at step 288, and periodically reports the operational evaluation of the medical device 14 to the user access device 254 at step 290.

The automated operational evaluation described above, provides a method of evaluating medical device 14 while in operation; thus eliminating the need to postpone evaluation until the medical device 14 is taken out of use. The real-time data collection capabilities of the MMU 12 and Monitor Pump 52 program allow the MMU 12 to determine medical device 14 performance including advanced statistical operations in order to provide quality control data sorting algorithms and aggregation of data and control for a PAN 113 (not shown). For example, consider a MMS 10 where multiple discreet single or multiple channel medical devices 14 (or channels) are connected to a single patient 110 (not shown). The Monitor Pump 52 program collects all medical device 14 information in real-time and then compares medical device 14 statistics to one another. Likewise, infuser channels can be compared to other infuser channels within the same multiple channel medical device or in other devices. Monitor Pump 52 program therefore can detect a "bad actor" if any one of the medical devices 14 or channels is operating at a level statistically lower or higher than the other medical devices 14 or channels. This statistical determination can be made by collecting and comparing the mean and standard deviation of appropriate data elements. This statistical determination can be performed selectably on any of the data that is routinely collected by the medical device 14 event log and any that may be acquired from the instrumentation of the medical device 14. For example, statistical determinations could be performed based on air alarm events, occlusion alarm events, battery usage data, screen response time, etc. MMU 12 then sends the operational evaluation message (including any relevant quality control alert) to an appropriate area (including but not limited to the computer 254) in a form that is appropriate for the particular alert (usually including but not limited to graphically or audibly). Additionally, operational evaluation message (including any relevant quality control alert) can be sent to any number of individuals including but not limited to the caregiver, a biomedical engineer, caregiver supervisor, and a doctor.

With reference to FIG. 17, the medical device 14 is designed as a multi-processor, where many features are not hardwired, but instead can be uniquely configured based on rules, the location of the medical device 14, etc. For example, the medical device 14 is designed to allow a customized display based on the Clinical Care Area (CCA) 253A or 253B the medical device 14 is located in and/or assigned too. An example of this would be the MMU 12 instructing the medical device 14 to have a display of a particular color or warning tones/volumes based on the location of the medical device 14 in the hospital, time of day, caregiver information, patient information, or the type of medication being supplied. For example, the patient information could include a patient diagnosis and/or a disease state. For example, alarm volumes and display brightness can be set lower in the pediatric clinical care area or at night than in the emergency room clinical care area or during the daytime.

With reference to FIG. 4, similarly, the medical device 14 is designed to allow a customized display based on user information supplied to the medical device 14 (from the MMU 12 for example) Such user based customized display could include changes in language preference, limited access depending on the security level of the caregiver 114, customizing the displayed information based on the training level of the individual or recent interactions therewith, and/or customizing an automated help function based on training level of the user or recent interactions therewith. The MMU 12 presents a user with a default view based on the user's role. The MMU 12 permits a default view for each role to be configurable in terms of the data detail presented. The MMU 12 allows a user with the appropriate privilege to set a particular presented view as the preferred or default starting view for that user following login. The MMU 12 allows a user to access databases and details based on role and privilege. The MMU 12 allows a user to access other views based on role and privilege. Each presented view includes: a common means of navigating among views, both summary and detail, access to privacy, security, and other policy statements, access to online help, and a logoff capability. Additionally, an emergency bypass (such as a pass-code) would be provided to bypass security restrictions in case of an emergency.

With reference to FIG. 22, another portion of the functional steps of the Monitor Pump 52 program in the MMU 12 and the corresponding Monitor Pump 130 program in the medical device 14 are shown in operation with the computer 254. The MMU 12 tracks and records actions taken by the caregiver 114 based on operational data reported from one or more medical devices 14. Just as the MMU 12 is capable of generating an operational evaluation of each medical device 14, the MMU 12 can likewise generating an operational evaluation of each caregiver 114 (not shown) at step 288. This operational evaluation of each caregiver 114 includes records of each caregiver's 114 actions (or, in some cases, inactions), sorting of these actions based on given criteria, and tracking of any trends in these actions. In general, these records of actions include any task lists, medication administration records, treatments, and other actions associated with the caregiver's 114 responsibilities. Such records of actions may combine medications administered, treatments, and other actions for multiple patients under the care of an individual caregiver. MMU 12 then sends the operational evaluation message (including any relevant quality control alert) to an appropriate area (e.g. to the computer 254 or caregiver supervisor's computer (not shown)) in a form that is appropriate for the particular alert (usually including but not limited to graphically or audibly). Additionally, operational evaluation message (including any relevant quality control alert) can be sent to any number of individuals including but not limited to the caregiver, a biomedical engineer, caregiver supervisor, and a doctor.

Additionally, the MMU 12 can instruct the medical device 14 to customized display 88 based on the operational evaluation message. Thus, the display 88 is adjusted by the MMU 12 based a determination that the caregiver 114 requires additional or different information displayed to improve caregiver 114 interaction with the medical device 14. For example, detailed step by step instructions can be placed on display 88, where the MMU 12 recognizes a caregiver 114 who is not familiar with a particular therapy, using the display 88 as the instruction means. Likewise, where the MMU 12 recognizes that a caregiver 114 has limited experience programming the medical device 14 (caregiver experience) or in previous interactions had made errors programming a particular function (caregiver error rate) or was a statistically longer than the norm at programming a particular function (caregiver response time), the MMU 12 instructs the medical device 14 to display pertinent training information.

In another embodiment best understood with reference to FIG. 4A, the medical device 14 is designed to act as a web server for the input device 32 or other similar devices within proximity to the medical device 14. In this embodiment, medical device 14 is equipped to supply the input device 32 web browser with medical device related information as well as non-medical device related information such as task lists, etc. Additionally, the medical device 14 displays a dual function screen having both a pump monitor screen portion and a web browser screen portion. Further, supplying the medical device 14 as a web server permits a remote web browser to associate with the medical device 14 to configure the medical device 14 or run diagnostics on the medical device 14.

With reference to FIGS. 2 and 4A, another portion of the Monitor Pump 52 program in the MMU 12 and the corresponding Monitor Pump 130 program in the medical device 14 is directed to cloning between medical devices 14. The medical devices 14 are designed to have wireless data sharing between each medical device 14 sufficient to permit cloning of all patient information between each medical device 14, and/or the multi-sequencing of a set of medical devices 14 without a hardwired connection. The MMU 12 adjudicates this cloning and/or multi-sequencing.

Whereas the invention has been shown and described in connection with the embodiments thereof, it will be understood that many modifications, substitutions, and additions may be made which are within the intended broad scope of the following claims. From the foregoing, it can be seen that the present invention accomplishes at least all of the stated objectives.

What is claimed is:

1. A method for evaluating the performance of multiple medical devices from a medication management unit, comprising the steps of:
   collecting operation information from each medical device at the medication management unit;
   generating a statistical measure of variations between the operation information from each medical device at the medication management unit; and
   analyzing the statistical measure at the medication management unit to determine if a select medical device has operation information indicating that the select medical device is operating at a level statistically different than non-select medical devices; and
   wherein the steps are at least partially performed while one of the medical devices is performing an infusion.

2. The method of claim 1, wherein the operation information is selected from a group consisting of air alarm events, occlusion alarm events, battery usage data, and screen response time.

3. The method of claim 1, further comprising the step of generating a quality control alert at the medication management unit where the statistical measure is outside a given threshold.

4. The method of claim 3, further comprising the step of sending the quality control alert to a clinician selected from a group consisting of a caregiver, a biomedical engineer, caregiver supervisor, and a doctor.

5. The method of claim 1, further comprising the step of collecting the operation information from each medical device in real-time.

6. A method for evaluating the performance of a medical device from a medication management unit, comprising the steps of:
- collecting operation information from the medical device at the medication management unit;
- generating a statistical measure of variations between the operation information from the medical device and a predetermined norm at the medication management unit; and
- analyzing the statistical measure at the medication management unit to determine if the medical device has operation information indicating that the medical device is operating at a level statistically different than the norm; and
- wherein the steps are at least partially performed while the medical device is performing an infusion.

7. A medication management system for evaluating the performance of multiple medical devices from a medication management unit, comprising:
- a plurality of medical devices in electronic communication with the medication management unit, each having a processor and a memory coupled to the processor, the memory containing programming code executed by the processor to output medical device specific operation information; and
- a medication management unit having a processing unit and a storage medium coupled to the processing unit, the storage medium containing programming code executed by the processing unit to perform steps comprising:
  - collecting operation information from each medical device at the medication management unit,
  - generating a statistical measure of variations between the operation information from each medical device at the medication management unit, and
  - analyzing the statistical measure at the medication management unit to determine if a select medical device has operation information indicating that the select medical device is operating at a level statistically different than the non-select medical devices; and
- wherein the steps are at least partially performed while one of the medical devices is performing an infusion.

8. A medication management system for evaluating the performance of a medical device from a medication management unit, comprising:
- a medical device in electronic communication with the medication management unit, the medical device having a processor and a memory coupled to the processor, the memory containing programming code executed by the processor to output medical device specific operation information; and
- a medication management unit having a processing unit and a storage medium coupled to the processing unit, the storage medium containing programming code executed by the processing unit to perform steps comprising:
  - collecting operation information from the medical device at the medication management unit,
  - generating a statistical measure of variations between the operation information from the medical device and a predetermined norm at the medication management unit, and
  - analyzing the statistical measure at the medication management unit to determine if the medical device has operation information indicating that the medical device is operating at a level statistically different than the norm; and
- wherein the steps are at least partially performed while the medical device is performing an infusion.

* * * * *